(12) United States Patent
Davis et al.

(10) Patent No.: US 9,534,206 B2
(45) Date of Patent: *Jan. 3, 2017

(54) CELL CARRIER, ASSOCIATED METHODS FOR MAKING CELL CARRIER AND CULTURING CELLS USING THE SAME

(71) Applicant: General Electric Company, Schenectady, NY (US)

(72) Inventors: Brian Michael Davis, Albany, NY (US); Kenneth Roger Conway, Clifton Park, NY (US); Evelina Roxana Loghin, Rexford, NY (US); Andrew Arthur Paul Burns, Niskayuna, NY (US); David Gilles Gascoyne, Niskayuna, NY (US); Scott Michael Miller, Clifton Park, NY (US)

(73) Assignee: General Electric Company, Niskayuna, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/461,860

(22) Filed: Aug. 18, 2014

(65) Prior Publication Data

US 2014/0356949 A1 Dec. 4, 2014

Related U.S. Application Data

(63) Continuation-in-part of application No. 12/970,735, filed on Dec. 16, 2010, and a continuation-in-part of application No. 13/839,049, filed on Mar. 15, 2013.

(51) Int. Cl.
*C12N 5/074* (2010.01)
*C12N 5/00* (2006.01)

(52) U.S. Cl.
CPC .......... *C12N 5/0696* (2013.01); *C12N 5/0068* (2013.01); *C12N 2533/30* (2013.01); *C12N 2533/90* (2013.01); *C12N 2535/10* (2013.01); *C12N 2537/00* (2013.01); *Y10T 156/1039* (2015.01)

(58) Field of Classification Search
None
See application file for complete search history.

(56) References Cited

U.S. PATENT DOCUMENTS

| | | |
|---|---|---|
| 4,801,475 A | 1/1989 | Halpern et al. |
| 4,906,237 A | 3/1990 | Johansson et al. |
| 5,284,766 A | 2/1994 | Okano et al. |
| 5,449,620 A | 9/1995 | Khillan |
| 5,707,859 A | 1/1998 | Miller et al. |
| 5,763,548 A | 6/1998 | Matyjaszewski et al. |
| 5,800,412 A | 9/1998 | Zhang et al. |
| 6,121,371 A | 9/2000 | Matyjaszewski et al. |
| 6,190,913 B1* | 2/2001 | Singh .............. 435/394 |
| 6,627,314 B2 | 9/2003 | Matyjaszewski et al. |
| 6,720,469 B1 | 4/2004 | Curtis et al. |
| 6,777,227 B2 | 8/2004 | Ricci et al. |
| 6,790,919 B2 | 9/2004 | Matyjaszewski et al. |
| 6,861,103 B2 | 3/2005 | Chang et al. |
| 7,052,776 B2 | 5/2006 | Fanta et al. |
| 7,354,704 B2 | 4/2008 | Malin et al. |
| 8,148,111 B2 | 4/2012 | Kurokawa et al. |
| 8,241,907 B2 | 8/2012 | Shogbon et al. |
| 2002/0028493 A1 | 3/2002 | de Bruijn et al. |
| 2002/0081726 A1 | 6/2002 | Russell et al. |
| 2003/0003554 A1 | 1/2003 | Miller et al. |
| 2003/0036196 A1 | 2/2003 | Okano et al. |
| 2003/0162287 A1 | 8/2003 | Yamamoto et al. |
| 2003/0219824 A1 | 11/2003 | Malin et al. |
| 2004/0214326 A1 | 10/2004 | Cousins et al. |
| 2005/0054101 A1 | 3/2005 | Felder et al. |
| 2006/0165625 A1 | 7/2006 | Verrall et al. |
| 2006/0205071 A1 | 9/2006 | Hasson et al. |
| 2008/0009064 A1 | 1/2008 | Ronfard et al. |
| 2008/0026464 A1 | 1/2008 | Borenstein et al. |
| 2008/0187995 A1 | 8/2008 | Murphy et al. |
| 2008/0199959 A1 | 8/2008 | Algotsson et al. |
| 2008/0208351 A1 | 8/2008 | Besenbacher et al. |
| 2009/0047260 A1 | 2/2009 | Van Dyke |

(Continued)

FOREIGN PATENT DOCUMENTS

| | | |
|---|---|---|
| DE | 102006012960 A1 | 9/2007 |
| EP | 0382214 B1 | 5/1995 |

(Continued)

OTHER PUBLICATIONS

CNMC; CNMC a Best Medical company, dosimetry phantoms; www.cnmcco.com, p. 1, accessed Aug. 3, 2015.*

(Continued)

*Primary Examiner* — Antonio Galisteo Gonzalez
(74) *Attorney, Agent, or Firm* — Eileen B. Gallagher

(57) ABSTRACT

A carrier for expansion of induced pluripotent stem cells is provided, wherein the carrier comprises a substrate comprising one or more outer surfaces, wherein the one or more outer surfaces are modified with gas plasma treatment, and one or more structured indentations on one or more of the outer surfaces. The carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm. A method of making the carrier, and culturing induced pluripotent stem cells using the same carrier are also provided.

27 Claims, 12 Drawing Sheets

(56) References Cited

U.S. PATENT DOCUMENTS

| | | | |
|---|---|---|---|
| 2009/0069904 A1 | 3/2009 | Picha | |
| 2009/0098183 A1 | 4/2009 | Detamore et al. | |
| 2009/0228027 A1 | 9/2009 | Yamanaka et al. | |
| 2009/0248145 A1* | 10/2009 | Chan et al. | 623/1.41 |
| 2009/0248157 A1 | 10/2009 | Dalby et al. | |
| 2009/0311735 A1 | 12/2009 | Crook et al. | |
| 2010/0093053 A1 | 4/2010 | Oh et al. | |
| 2010/0124781 A1 | 5/2010 | Nelson | |
| 2010/0136647 A1 | 6/2010 | Algotsson et al. | |
| 2010/0197013 A1 | 8/2010 | Kamp et al. | |
| 2010/0291674 A1 | 11/2010 | Beese et al. | |
| 2010/0304482 A1 | 12/2010 | Deshayes et al. | |
| 2010/0330674 A1 | 12/2010 | Rubinsztajn et al. | |
| 2011/0027889 A1 | 2/2011 | McCarthy et al. | |
| 2011/0076764 A1 | 3/2011 | Rubinsztain et al. | |
| 2011/0104732 A1 | 5/2011 | Lucic et al. | |
| 2011/0129919 A1 | 6/2011 | Oh et al. | |
| 2011/0160869 A1 | 6/2011 | Duch et al. | |
| 2011/0207209 A1 | 8/2011 | Hammons et al. | |
| 2011/0207216 A1 | 8/2011 | Martin et al. | |
| 2011/0275154 A1 | 11/2011 | Martin et al. | |
| 2012/0045830 A1 | 2/2012 | Green et al. | |
| 2012/0052579 A1 | 3/2012 | Shannon et al. | |
| 2012/0058556 A1 | 3/2012 | Fabian et al. | |
| 2012/0058561 A1 | 3/2012 | Sato | |
| 2012/0156773 A1 | 6/2012 | Smith et al. | |
| 2012/0156777 A1 | 6/2012 | Rangarajan et al. | |
| 2012/0219531 A1 | 8/2012 | Oh et al. | |
| 2014/0051163 A1 | 2/2014 | Healy et al. | |

FOREIGN PATENT DOCUMENTS

| | | |
|---|---|---|
| GB | 1079391 A | 8/1967 |
| JP | 2004018556 A | 1/2004 |
| JP | 2010057485 A | 3/2010 |
| JP | 2010136706 A | 3/2010 |
| WO | 9932595 A1 | 1/1999 |
| WO | 0070406 A1 | 11/2000 |
| WO | 0162803 A2 | 8/2001 |
| WO | 0192359 A1 | 12/2001 |
| WO | 03055967 A1 | 7/2003 |
| WO | 2004090506 A3 | 6/2005 |
| WO | 2006033935 A2 | 3/2006 |
| WO | WO 2007125288 A1 * | 11/2007 |
| WO | 2008106771 A1 | 9/2008 |
| WO | 2008140295 A1 | 11/2008 |
| WO | 2009034186 A2 | 3/2009 |
| WO | WO 2009105570 A2 * | 8/2009 |
| WO | 2010094944 A1 | 8/2010 |
| WO | 2011106032 A1 | 9/2011 |
| WO | 2011147930 A1 | 12/2011 |
| WO | 2012069841 A1 | 5/2012 |

OTHER PUBLICATIONS

Van Kooten et al.; Plasma-treated polystyrene surfaces: model surfaces for studying cell-biomaterial interactions; Biomaterials; vol. 25, pp. 1735-1747 (2004).*

Khorasani et al., "Plasma Surface Modification of Poly (I-lactic acid) and Poly (lactic-co-glycolic acid) Films for Improvement of Nerve Cells Adhesion", Radiation Physics and Chemistry, pp. 280-287, vol. 77, Issue 3, Mar. 2008.

Kohen et al., "Characterization of Matrigel Interfaces during Defined Human Embryonic Stem Cell Culture", Biointerphases, pp. 69-79, vol. 4, Issue 4, Dec. 2009.

Satoh et al, "Cultivation of Human Induced Pluripotent Stem Cells with Controlled Aggregate Size and Geometrical Arrangement by Inverting Microwell Array Chip", 17th International Conference on Miniaturized Systems for Chemistry and Life Sciences, pp. 1701-1703, Oct. 27-31, 2013.

Manbachi et al. "Microcirculation within Grooved substrates regulates Cell positioning and Cell Docking inside Microfluidic Channels", Lab Chip, May 2008, pp. 747-754.

Melinex 454, XP-002672166, Downloaded from the Internet:<http://www.fly-supply.com/Melinex-Films/Melinex-454/Det> on Mar. 22, 2012, 1 Pages.

BD Biosciences, BD BIOCOAT—DISH 35MM PLL 5PAC 20CAS, 2010, Downloaded from the Internet:<http://www.bdbiosciences.com/ptProduct.jsp?prodId=36494> on Mar. 16, 2012, 1 Pages.

Collignon et al., "Integrity™ Xpansion™ Multiplate Bioreactor: The Scalable Solution for Adherent Stem Cell Expansion", ATMI LifeSciences, 2010, 1 Page.

Focke et al. "Lab-on-a-Foil: microfluidics on thin and flexible films", Lab on a Chip, vol. 10, Mar. 19, 2010, pp. 1365-1386.

Fujita et al., "Time-lapse observation of cell alignment on nanogrooved patterns", Journal of Royal Society Interface, vol. 6, Feb. 25, 2009, pp. S269-S277.

Funakoshi General Catalog 2005-2006 devices edition, pp. viii—ix, Dec. 22, 2005, 8 Pages.

Moeller et al., "A microwell Array system for stem cell culture", Nov. 14, 2007, pp. 752-763.

Lindstrom et al., "High-Density Microwell Chip for Culture and Analysis of stem cells", PLoS ONE, vol. 4, Issue No. 9, Sep. 2009, pp. 1-9.

Cha et al., "Construction of Functional Soft Tissues From Premodulated Smooth Muscle Cells Using a Bioreactor System", Artificial Organs, vol. 30, Issue No. 9, Sep. 2006, pp. 704-707.

Cha et al., "Time-dependent Modulation of Alignment and Differentiation of Smooth Muscle Cells Seeded on a Porous Substrate Undergoing Cyclic Mechanical Strain", Artificial Organs, vol. 30, Issue No. 4, Apr. 2006, pp. 250-258.

Korin et al., "Design of Well and Groove Microchannel Bioreactors for Cell Culture", Biotechnology and Bioengineenng, vol. 102, Issue No. 4, May 1, 2009, pp. 1222-1230.

Lee et al., "Response of human chondrocytes on polymer surfaces with different micropore sizes for tissue-engineered cartilage", J Appl Polym Sci., vol. 92, 2004, pp. 2784-2790.

Jiang et al., "Fabrication of plastic microlens arrays using hybrid extrusion rolling embossing with a metallic cylinder mold fabricated using dry film resist", Optics Express, vol. 15, Issue No. 19, Jan. 1, 2007, pp. 12088-12094.

Khabiry et al.; "Cell Docking in Double Grooves in a Microfluidic channel", 2009 , 9 Pages.

McMurray et al., "Nanoscale surfaces for the long-term maintenance of mesenchymal stem cell phenotype and multipotency", Nature Materials, vol. 10, Aug. 2011, 8 Pages.

Kessel et al., "Thermoresponsive PEG-based polymer Layers: Surface characterization with AFM force measurements", Langxmuir, vol. 26, Issue No. 5, 2010, pp. 3462-3467.

Thormann et al., "Interactions between a Polystyrene Particle and Hydrophilic and Hydrophobic Surfaces in Aqueous Solutions", Langmuir, vol. 24, Issue No. 14, 2008,, pp. 7278-7284.

Huang et al., "Fast fabrication of integrated surface-relief and particle-diffusing plastic diffuser by use of a hybrid extrusion roller embossing process", Optics Express, vol. 16, Issue No. 1, Jan. 2008, pp. 440-447.

Ueda et al., "Substrates for Human Pluripotent Stem Cell Cultures in Conditioned Medium of Mesenchymal Stem Cells", Journal of Biomaterials Science, Polymer Edition, vol. 23, Issue No. 1-4, Apr. 13, 2012, pp. 153-165.

Velten et al., "Roll-to-Roll Hot Embossing of Microstructures", Design Test Integration and Packaging of MEMS/MOEMS (DTI P), 2010, pp. 326-331.

Velten et al., "Investigations on reel-to-reel hot embossing", The international journal of advanced manufacturing technology, springer, berlin, DE, vol. 1-4, 24, Feb. 2009, pp. 73-80.

Wave Bioreactor Catalog2006, Wave Europe, 2006, pp. 1-13.

Yeo et al., "Micro-fabrication of polymeric devices using hot roller embossing"; Microelectronic Engineering, vol. 86, Dec. 2008, pp. 933-936.

International Search Report and Written Opinion from related PCT Application No. PCT/EP2011/073065 dated Apr. 23, 2012, 8 Pages.

International Search Report and Written Opinion from related PCT Application No. PCT/EP2011/073061 dated May 2, 2012, 9 Pages.

International Search Report and Written Opinion from related PCT Application No. PCT/EP2011/073066 dated May 7, 2012, 8 Pages.

(56) References Cited

OTHER PUBLICATIONS

International Search Report and Written Opinion issued in connection with relatedPCT Application No. PCT/EP2011/073064 on May 9, 2012, 9 Pages.
Unofficial English translation of Office Action and Search Report issued in connection with related CN Application No. 201180060701.9 on May 6, 2014, 5 Pages.
Unofficial English translation of Office Action issued in connection with related CN Application No. 201180060701.9 on Jul. 6, 2015, 3 Pages.
Unofficial English translation of Office Action issued in connection with related JP Application No. 2013543815 on Dec. 15, 2015, 6 Pages.

* cited by examiner

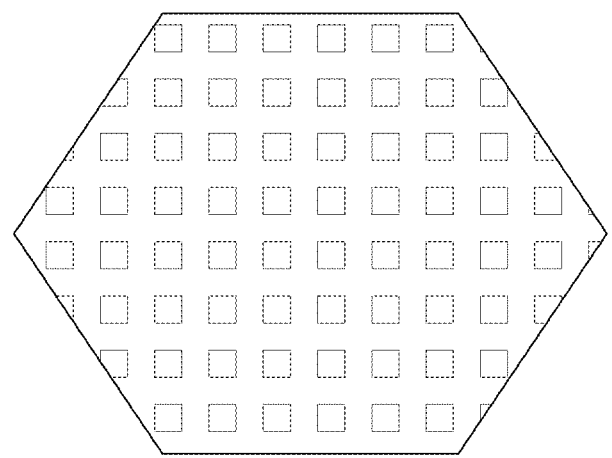
FIG. 6A
 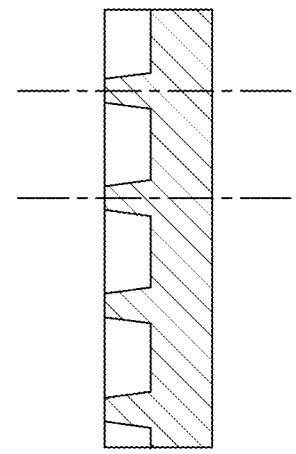
FIG. 6B  FIG. 6C

CELL CARRIER, ASSOCIATED METHODS FOR MAKING CELL CARRIER AND CULTURING CELLS USING THE SAME

CROSS REFERENCE TO RELATED APPLICATIONS

This application is a continuation-in-part of U.S. patent application Ser. No. 12/970,735, entitled "Cell carrier, associated methods for making cell carrier and culturing cells using the same", filed Dec. 16, 2010 and U.S. patent application Ser. No. 13/839049, entitled "Cell carrier, associated methods for making cell carrier and culturing cells using the same", filed Mar. 15, 2013 which are herein incorporated by reference.

FIELD

The invention relates to cell carriers for culturing induced pluripotent stem cells (iPSC), including human induced pluripotent stem cells (hiPSC) and associated methods for making and using the cell carriers. More particularly, the invention relates to polymer based cell carriers with surface modification to expand undifferentiated induced pluripotent stem cells.

BACKGROUND

Induced pluripotent and multipotent stem cells have the potential to revolutionize various therapeutic applications, especially in the fields of regenerative medicine and pharmaceutical development. One of the obstacles for stem cell-based therapy is the requirement of large number of cells, which can be met by expanding stem cells in a large scale. A number of technical hurdles remain for expansion of such cells using currently available substrates for cell culture using a bioreactor.

Bioreactors have long been practiced as the preferred scale-up method for cell culture. The use of microcarriers for culturing adherent cells is common in industrial practice, such as in bioprocessing. Typical bioreactor vessels employ some means of agitation, such as internal impellers, rocking or shaking mechanisms to suspend the cells and allow mass transfer of nutrients, oxygen and metabolic waste products. The agitation can subject cells to high degrees of flow-induced stress that can damage cells or alter the cell phenotype, especially sensitive ones such as stem cells. A carrier that protects stem cells from agitation-induced damage and provides better stem cell recovery has recently been developed. One of the biggest remaining technological needs is control over stem cell differentiation, both in terms of suppressing spontaneous differentiation as well as enhancing directed differentiation.

Stem cells are inherently susceptible to differentiation based on their local environment, which typically generates the appropriate cell types for the current stage of development or produces cells for generating particular tissues. To control differentiation, the major focus has been on biochemical cues for stem cell growth and differentiation, leading to a great variety of specialized media and surface treatments for the maintenance of stem cell pluripotency or induction of differentiation. Originally, many induced pluripotent stem cells are grown in a co-culture with mouse embryonic feeder cells (MEF) which conditioned the environment to support induced pluripotent growth, however this leads to the potential for xeno-contamination and adds to the inherent biological variability of the system. To avoid contamination, a combination of surface treatments with extracellular matrix proteins, different media formulations or other surface-modifiers have been employed to achieve similar results, though the surface coating of extracellular matrix proteins remains a biologically variable source of growth signals for non-recombinant protein mixtures.

Therefore, cell carriers, which provide protection from flow induced stress and easy separation of the carriers from cells, are an unmet need in the art. The development of cell carriers that facilitates stem cell attachment, proliferation and release, while maintaining stem cell pluripotency or directing differentiation under reduced shear forces is highly desired.

BRIEF DESCRIPTION

In one embodiment, a carrier for expansion of induced pluripotent stem cells, comprises a substrate comprising one or more outer surfaces; wherein the one or more outer surfaces are modified with gas plasma treatment, and wherein one or more structured indentations on one or more of the outer surfaces, and the carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm In another embodiment, a carrier for expansion of induced pluripotent stem cells, comprises a substrate comprising one or more outer surfaces; wherein the one or more outer surfaces comprise a biomolecular coating, and wherein one or more structured indentations on one or more of the outer surfaces, and the carrier has a length at least about 0.2 mm, a width at least about 0.2 mm, and a height in a range from about 0.05 mm to 1.2 mm and each of the structured indentations has a major axis in a range from about 0.1 to 0.5 mm, a minor axis in a range from about 0.1 mm to 0.5 mm and a depth in a range from about 0.025 mm to about 0.5 mm.

In another embodiment, a carrier for expansion of induced pluripotent stem cells, comprises a substrate comprising one or more outer surfaces modified with one or more of corona discharge treatment, gas plasma treatment, or chemical functionalization to form modified surfaces; and a biomolecular coating disposed on one or more of the modified surfaces, wherein one or more structured indentations on one or more of the outer surfaces, and the carrier has a length at least about 0.2 mm, a width at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm.

In a method for expanding induced pluripotent stem cells, wherein the method comprises providing a carrier for expansion of induced pluripotent stem cells, comprising a substrate comprising one or more outer surfaces modified with one or more of corona discharge treatment, gas plasma treatment, coating, or chemical functionalization to form modified surfaces; and a biomolecular coating disposed on the modified surfaces, wherein one or more structured indentations on one or more of the outer surfaces, wherein the carrier has a length at least about 0.2 mm, a width at least about 0.2 mm, and a height in a range from about 0.05 mm to 1.2 mm and each of the structured indentations has a major axis in a range from about 0.1 mm to 0.5 mm, minor axis in a range from about 0.1 mm to 0.5 mm and depth in a range from about 0.025 mm to about 0.5 mm, seeding and expanding the induced pluripotent stem cells on the carrier.

One embodiment of a method of making carriers for expanding induced pluripotent stem cells, comprises a) providing one or more flat polymer films; b) forming on the flat polymer films, on one or more sides, one or more structured indentations; c) cutting the treated polymer film into a plurality of portions to form carriers; and d) imparting a surface treatment to the film comprising one or more of corona discharge treatment, gas plasma treatment, chemical functionalization or coating.

In another embodiment of method of making carriers for expanding induced pluripotent stem cells, wherein the method comprises a) providing one or more polymer films comprising one or more structured indentations on one or more sides of the films; b) cutting the treated polymer film into a plurality of portions to form carriers; and c) imparting a surface treatment to the carriers comprising one or more of corona discharge treatment, gas plasma treatment, chemical functionalization, coating or combinations thereof.

DRAWINGS

These and other features, aspects, and advantages of the present invention will become better understood when the following detailed description is read with reference to the accompanying drawings in which like characters represent like parts throughout the drawings, wherein:

FIG. 1A is an image of a carrier of the invention comprising a plurality of indentations showing dimensions of the carrier. FIG. 1B is an image of the same carrier showing dimensions of each indentation.

FIG. 2A is an image of a carrier of the invention comprising one indentation on one side of the base. FIG. 2B is an image of a carrier of the invention comprising one indentation each on two opposing sides of the base. FIG. 2C is a scanning electron microscope (SEM) image of a carrier of the invention comprising a plurality of indentations on one side of the base. FIG. 2D is an SEM image of a carrier of the invention comprising a plurality of indentations on both sides of the base.

FIG. 6 A represents schematic drawing of hexagonal embossed carrier with specific dimension. FIG. 6B is a cross sectional view of a carrier and FIG. 6C is a magnified view of the cross sectional side view of the carrier with specific dimension.

Figure 7:
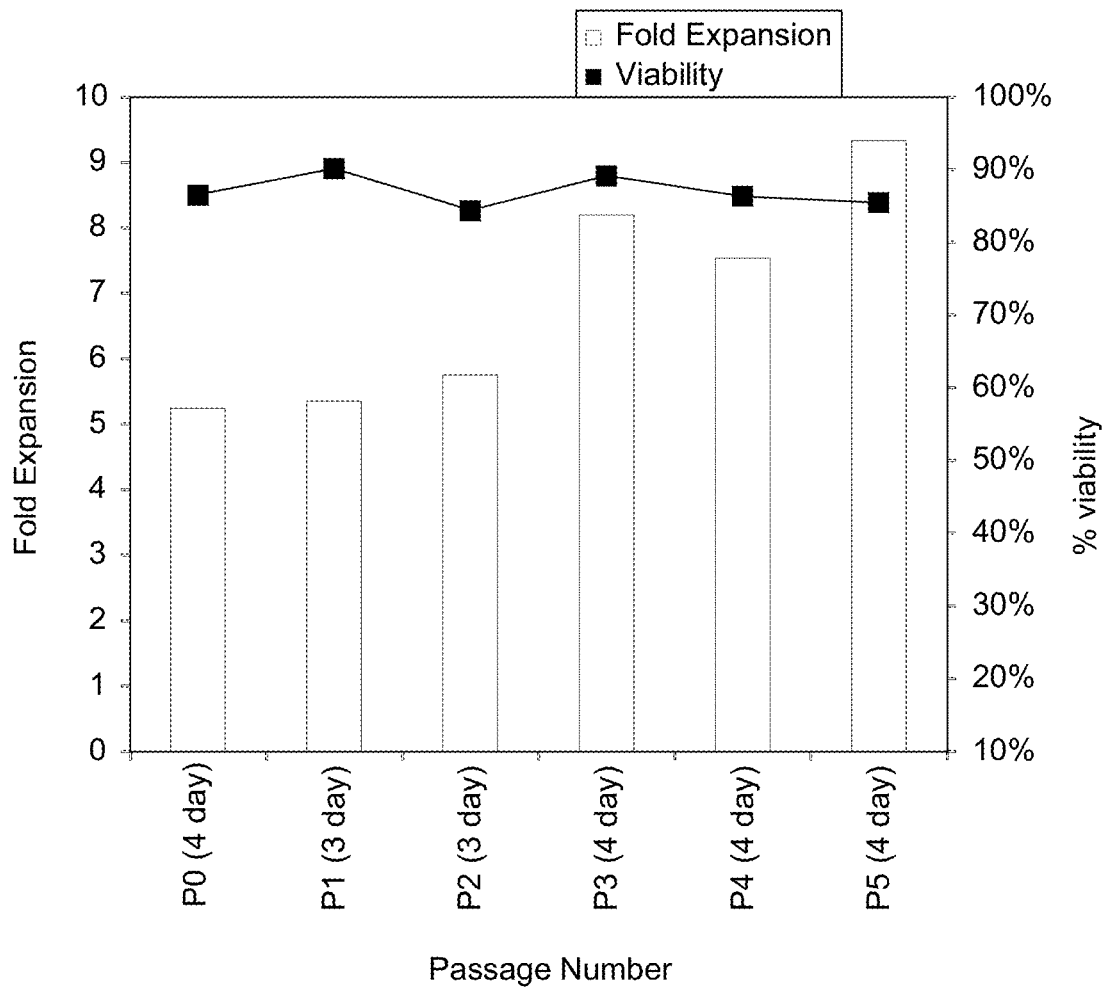

FIG. 7 represents bar graphs illustrating expansion and viability of NL-5 cells expanded on 100 cm$^2$ carriers of the invention in the spinner flask for 5 serial passages, each passage representing either 3 or 4 days expansion.

Figure 8B:
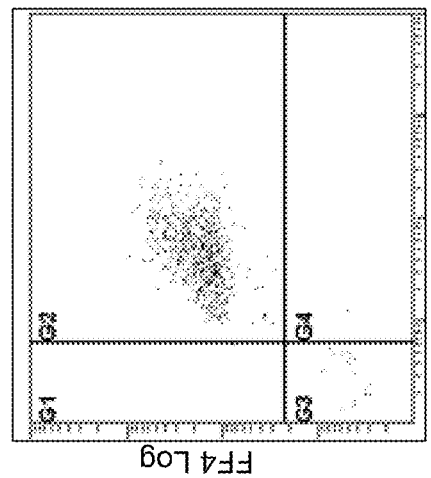
Figure 8A:
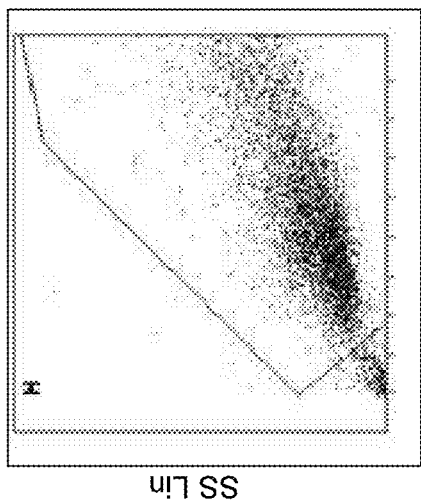
Figure 8D:
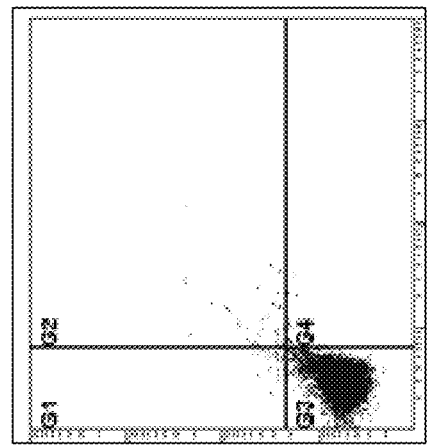
Figure 8C:
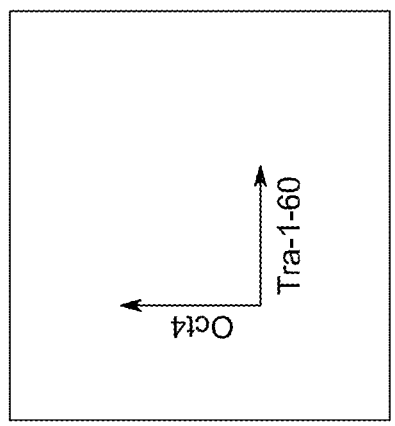

FIG. 8A to 8D show a flow cytometric evaluation of the pluripotency markers Oct4 and Tra-1-60 expression on NL-5 cells serially passaged on the carriers of the invention in stirred tank reactors. FIG. 8A shows the axis for Oct4 and Tra-1-60, FIG. 8B shows forward scatter and side scatter properties of the cells, FIG. 8C is a negative control using isotype antibodies, and FIG. 8D shows pluripotency marker expression from cells grown for 5 passages on the carriers of the invention.

Figure 9:
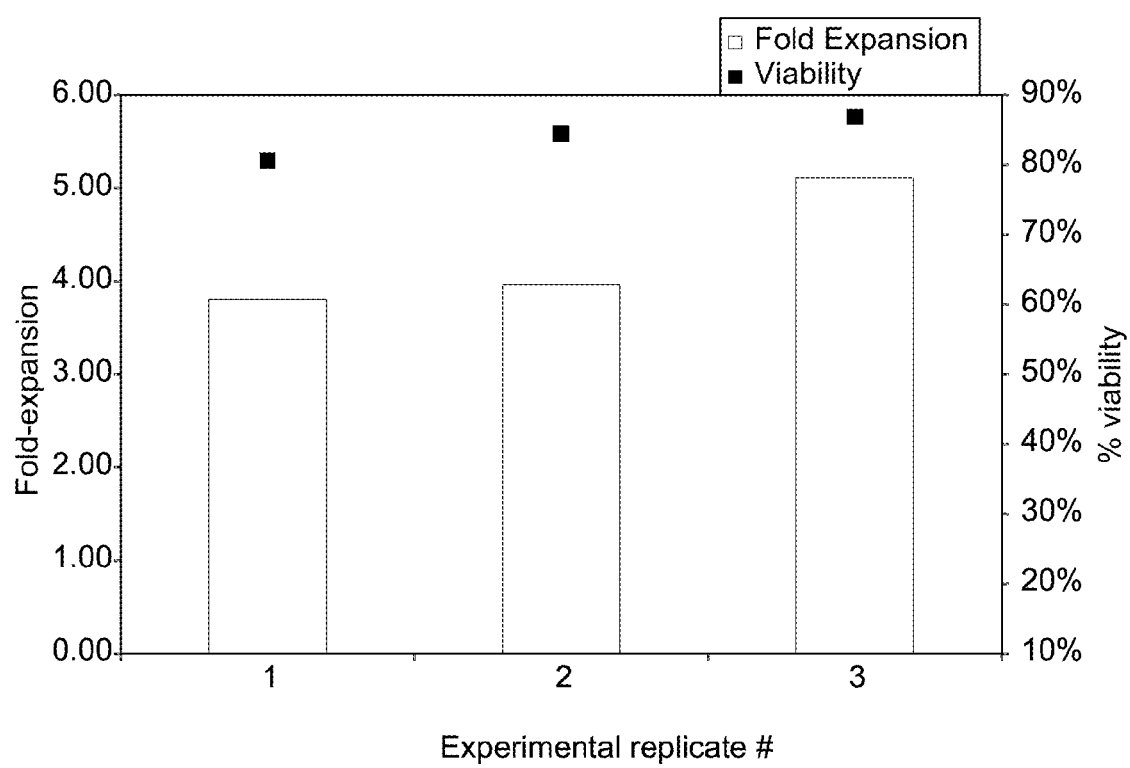

FIG. 9 represents bar graphs illustrating expansion and viability of NL-5 cells expanded on 500 cm$^2$ carriers of the invention in the spinner flask for 3 or 4 days.

DETAILED DESCRIPTION

One or more of the embodiments of the invention relate to cell carriers for culturing induced pluripotent or multipotent stem cells, wherein the carriers are suspended in a bioreactor. The carrier may be modified by a surface treatment for better cell attachment, controlled growth and ease of release. The surface treatment may include applying a coating material, gas plasma treatment, corona discharge treatment or combinations thereof.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

A "carrier" or "carrier for growing cells", as referred to herein, is a support for adhering and culturing cells. The carrier may have indentations on it. Suitable materials of the carrier may include, but are not limited to, polymers, copolymers or blends of polymers. The carrier may further be coated with a suitable coating material for effective cell adherence and proliferation. The carrier may have one or more surface treatments, such as gas plasma treatment.

A "major axis", as referred to herein, is the longest dimension of each indentation present on the carrier surface. For example, for a rectangular indentation, length of the indentation is referred as the 'major axis'. A "minor axis", as referred to herein, refers to a dimension other than the longest dimension, of each indentation present on the carrier surface. For example, for a rectangular indentation, width of the indentation is referred as the 'minor axis'. For example, the major axis is the same as the minor axis for a square indentation as the length and width are same, as shown in FIG. 1B, 14 and 16 respectively, the major axis is a diameter for a circular indentation as shown in FIG. 2B, 14, major axis is length for a rectangular indentation, and major axis is the major axis of an elliptical indentation.

An "aspect ratio", as referred to herein, is a ratio of depth to major axis of each structured indentation. For example, an aspect ratio for a circular indentation is a ratio of depth to diameter.

A "biomolecular coating", as referred to herein, is a coating comprising molecules either derived from biological system or synthetically made. The biomolecular coating may comprise biological proteins, recombinant proteins, natural peptides, synthetic peptides, oligomers, nucleic acids, or carbohydrates.

Embodiments of the carrier in suspension comprise one or more outer surfaces; wherein one or more of the outer surfaces of the carrier comprise one or more structured indentations and the surfaces are sometimes modified with gas plasma treatment to enhance cytophilicity. The invention also comprises methods of making the carrier, and methods and kits for culturing induced pluripotent stem cells using the carriers for cell growth.

One or more embodiments of a carrier for expansion of induced pluripotent stem cells comprise a substrate comprising one or more outer surfaces where the surfaces are modified with gas plasma treatment. The substrate further comprises one or more structured indentations on one or more of the outer surfaces, where the carrier has a length of at least about 0.2 mm, a width of at least about 0.2 mm, and a height in a range from about 0.05 mm to 1.2 mm and each of the structured indentations has a major axis in a range from about 0.1 mm to 0.5 mm, a minor axis in a range from about 0.1 mm to 0.5 mm and a depth in a range from about 0.025 mm to about 0.5 mm.

Figure 1A:
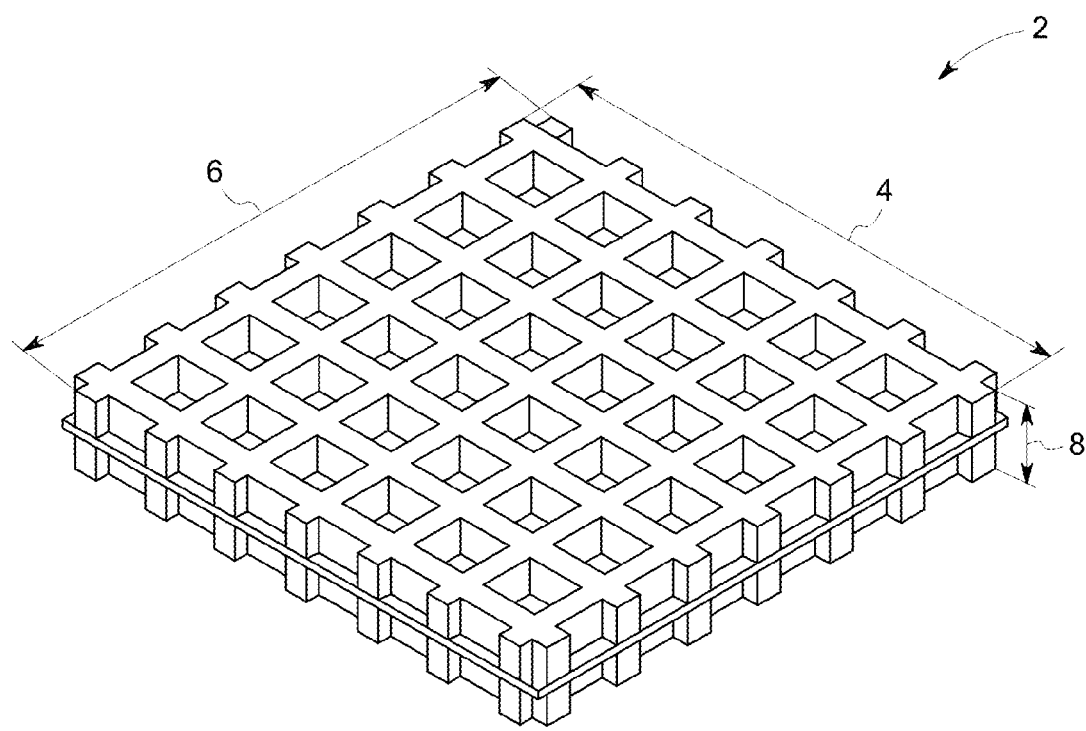
Figure 1B:
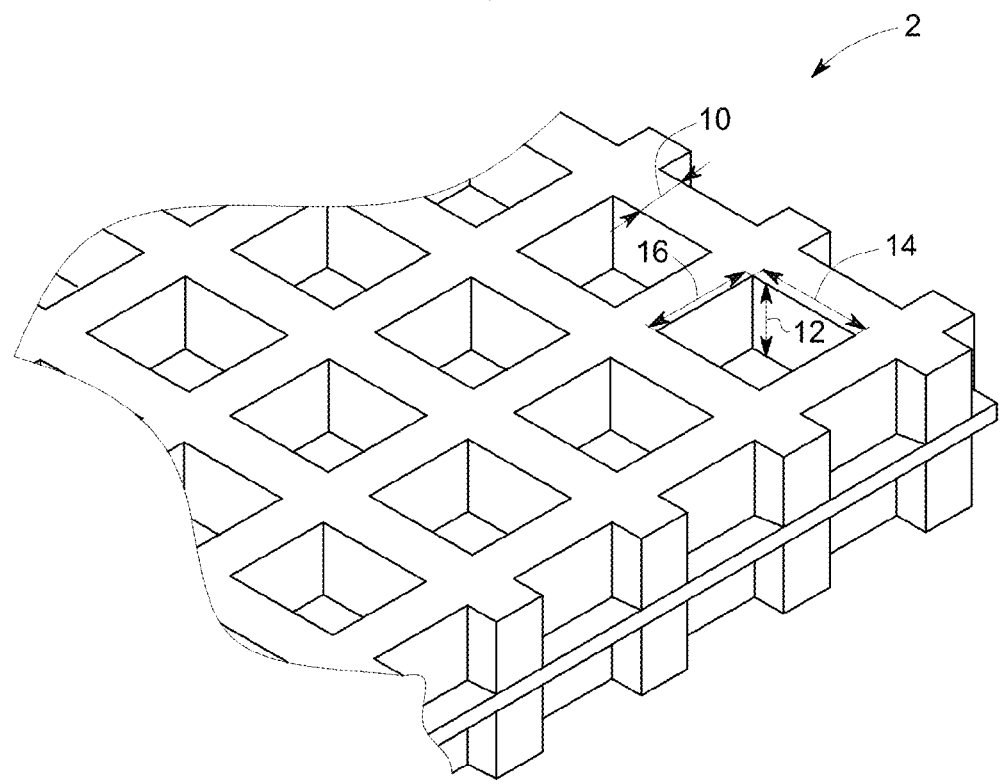

As noted, the carrier for growing induced pluripotent stem cells comprises one or more outer surfaces; and one or more structured indentations in one or more of the outer surfaces, wherein the carrier 2, as shown in FIG. 1A, has a length 4 of at least about 0.2 mm, a width 6 of at least about 0.2 mm, and a height 8 in a range from about 0.05 mm to 1.2 mm In some embodiments, the carrier has a length 4 in a range from about 0.2 mm to 15 mm, a width 6 in a range from about 0.2 mm to 15 mm, and a height 8 in a range from about 0.05 mm to 1.2 mm. In some embodiments, the carrier has a width and length from about 0.2 to 25 mm. In some embodiments, the wall-thickness 10 of the carrier is in a range from about 0.05 mm to 2 mm. In some embodiments, the carrier comprises a surface 3, wherein the surface is treated with one or more of corona discharge treatment, gas plasma treatment, chemical functionalization or coating.

Embodiments of the structured indentations, as shown in FIG. 1B, comprise a depth 12, a major axis 14, and a minor axis 16, wherein the major axis 14 of an indentation is in a range from about 0.1 mm to 0.5 mm, the minor axis 16 is in a range from about 0.1 mm to 0.5 mm, and the depth 12 is in a range from about 0.025 mm to about 0.5 mm. The wall-thickness 10 is in a range from about 0.05 mm to 2 mm. As used herein the term, 'depth' of an indentation refers to the depth of the inner wall of each indentation. As used herein, the term 'wall-thickness' refers to a thickness of a single wall for a carrier with single indentation, or thickness of each of the multiple walls for the carrier with a plurality of structured indentations as shown in FIG. 1B. Each of the structured indentations has an aspect ratio in a range from about 0.1 to about 1.5. In some embodiments, the carrier comprises a surface 3, wherein the surface is treated with one or more of corona discharge treatment, gas plasma treatment, chemical functionalization or coating.

Figure 2A:
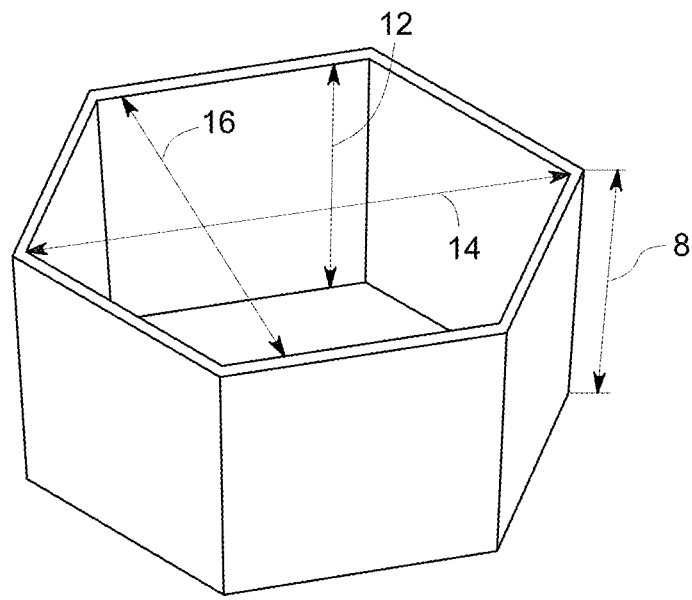
Figure 2B:
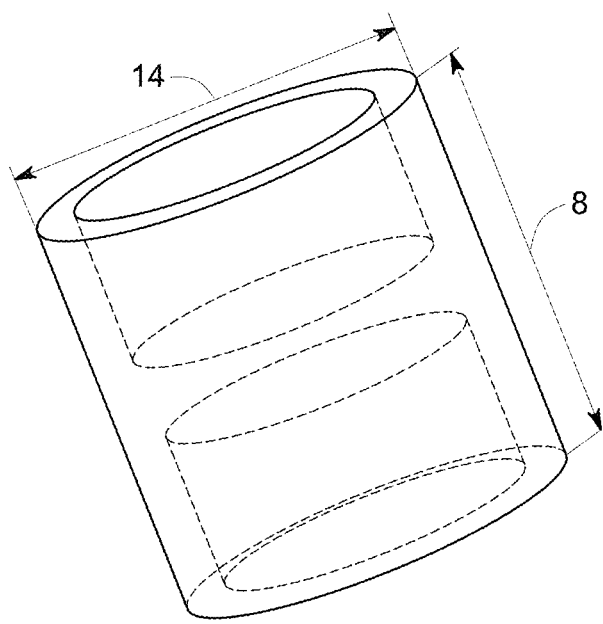

In one embodiment, the carrier may comprise one indentation on at least one surface of the carrier as shown in FIG. 2A. In this embodiment, the carrier is a 'cup' like structure on one outer surface of the base with a continuous wall surrounding the base of the carrier. In an alternate embodiment, the carrier may comprise one indentation on each of the surfaces of the carrier as shown in FIG. 2B. In this embodiment, the carrier has two 'cup' like structures on opposing outer surfaces of the base with a continuous wall surrounding the cups. This carrier may be useful for specific cell culture conditions or for specific cell-types. The single carrier (FIG. 2A and 2B) has a length in a range from about 0.1 mm to 15 mm, a width in a range from about 0.1 to 15 mm, and a height 8 in a range from about 1 mm to 10 mm, and a wall-thickness 10 of the carrier in a range from about 0.05 mm to 2 mm. In case of a single 'cup' (FIG. 2A) or two 'cups' on opposing sides of the base (FIG. 2B), has a length that is same as the major axis 14 as shown in FIG. 2A and 2B, a width that is same as the minor axis 16, and the cup has a depth 12, as shown in FIG. 2A.

Figure 2C:
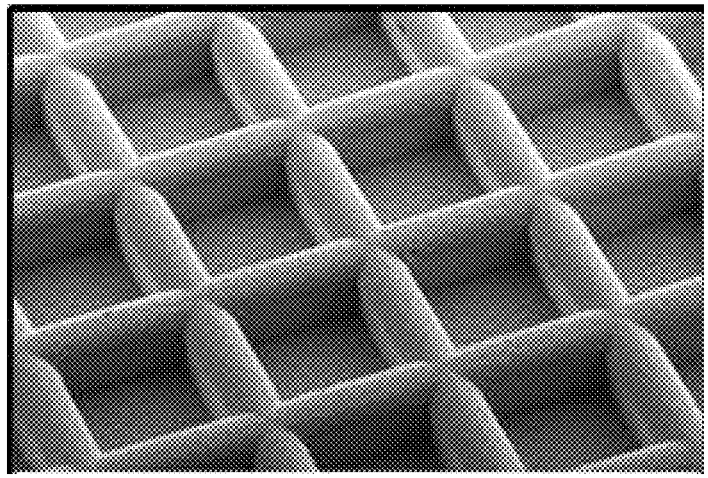
Figure 2D:
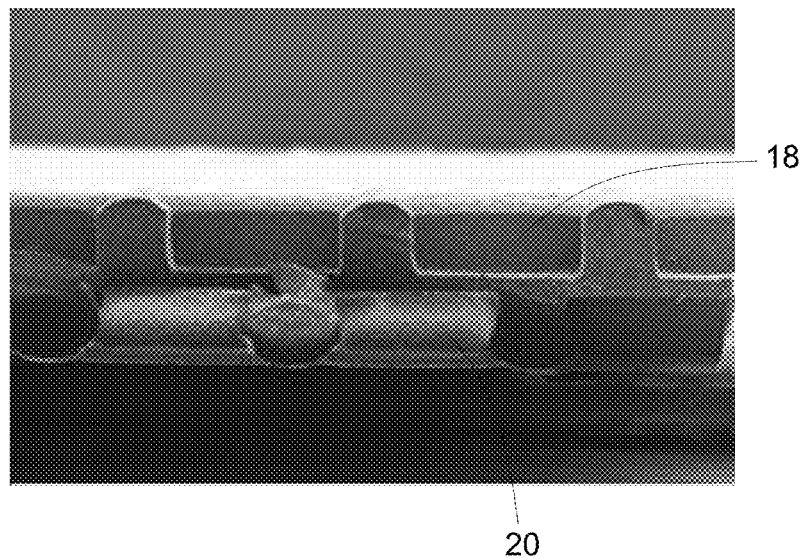

In some embodiments, the carrier comprises at least one surface for growing induced pluripotent stem cells, wherein more than one structured indentation is present on the surface, for example, the carrier has a plurality of structured indentations on one outer surface of the base, as shown in the SEM image in FIG. 2C. The carrier, in one embodiment, comprises at least two outer surfaces. In this embodiment, more than one structured indentation is formed on each of the outer surfaces, such as 18 and 20 are the structured indentations on the upper and lower surface respectively, as shown in FIG. 2D. In this embodiment, the carrier has a plurality of indentations on opposing outer surfaces of the base (FIG. 2D).

In some embodiments, the carrier has a substantially planar disc-like structure. As used herein, 'substantially planar disc', refers to a disc, which provides a planar surface area for growing cells. The shape of the carrier may be polygonal. In one or more embodiments, the shape of the carrier may vary, for example, the carrier may have an overall perimeter that is circular, elliptical, triangular, rectangular, square, pentagonal, or hexagonal shape.

The disc like-structure of the carrier may provide higher surface area per unit volume for culturing cells, relative to, e.g. spherical structures. The shape and size of the carrier may also allow about 2 to 50-fold of hiPSC expansion per passage. In some embodiments, the carrier allows about 2 to 20-fold of hiPSC expansion per passage. In one embodiment, the hiPSC expansion per passage is about 10-fold. In another embodiment, the hiPSC expansion per passage is about 20-fold. Efficient separation of enzymatically (e.g. release using trypsin or accutase, etc.) or chemically released (EDTA, Cell Dissociation Buffer) cells from the carriers is facilitated due to the significant size difference between the cells (~6 to 8 micron) and the carriers (larger than 0.2 mm) Released cells may be separated from the carriers via simple filtration, or separation of suspended cells in the supernatant after allowing the carriers to gravity settle.

The structured indentation has a wall that protrudes normal to the outer surface of the carrier, as shown in FIGS. 1A, 1B, 2A, and 2B. The wall height is chosen to balance the various requirements of the carrier, for example, a lower wall (i.e. shallow indentation) allows higher packing density of carriers per unit volume, and therefore can provide higher cell yield per unit volume of reactor. Moreover, transport of oxygen, nutrients and metabolic waste to/from the cells is facilitated at lower wall height (i.e. shallower indentations). However, a higher wall (i.e. deeper indentation) can offer higher degrees of protection from hydrodynamic forces arising due to agitation inside the bioreactor. Further, a higher wall or deeper indentation can provide a microenvironment that prevents dilution of any cell-secreted molecules. This may be advantageous if cell-cell signaling or autocrine factors are a desired part of the cell culture or processing operations. The desired range of the height of the wall projected above the plane of the carrier is therefore optimized with these factors in mind, in a range from 0.05 mm to 1.2 mm; in some embodiments from about 0.05 mm to about 0.5 mm, or in some embodiments, from about 0.15 mm to about 0.25 mm In use, the carriers are maintained in suspension inside a bioreactor, comprising a fluid having a convective motion that generates sufficient transport of nutrients and oxygen to cells. The cells adhere to the surface of the structured indentations having a flat or curved wall of sufficient height such that the effect of fluid-induced hydrodynamic stress on the cells is minimized The carrier comprises an optimum depth of indentations, balancing the needs of the adherent cells providing access to nutrients and metabolites, while protecting the cells from exposure to hydrodynamic shear generated by fluid motion.

Unlike other adherent cells, the induced pluripotent stem cells (iPSCs) may adhere poorly to a polymeric surface due to cell phenotype or culture conditions. A surface treatment can be employed to improve the cell attachment and limit spontaneous differentiation. The surface treatment may include plasma treatment, coatings, surface functionalizations or combinations thereof. The plasma treated surface may result in faster and more robust cell attachment on the cell carriers and result in higher cell yields compared to un-treated carriers.

As noted, the one or more surfaces of the carriers may be modified with plasma treatment. Plasma treatment may result in increasing hydrophobicity or hydrophilicity. In some embodiments, the polymer-based carrier surfaces are further modified with functional groups or coatings to enable better cell attachment and growth. Plasma treatments may be broadly categorized into two types: atmospheric plasma treatment in which an electrical energy source is combined with atmospheric gases to create reactive plasma, known as corona discharge treatment. The other treatment comprises vacuum plasma treatment wherein an electrical or a radio frequency energy source is used in combination with a vacuum chamber containing gases including oxygen, nitrogen, nitrous oxide, carbon monoxide, carbon dioxide, argon or combinations thereof to create a reactive plasma. In some embodiments, a surface treatment is imparted to the embossed polymer film comprising one or more of corona discharge treatment, gas plasma treatment, chemical functionalization, coating or combinations thereof.

In one or more embodiments, the surface modification may be achieved via plasma treatment. The plasma treatment on each of the surfaces may modify the surface property of the carriers, e.g. hydrophobicity, hydrophilicity or wettability. Wettability may be quantified by contact angle measurements. The increased hydrophilicity of plasma treated carriers is known to improve cell attachment and growth compared to growth on untreated polymer surfaces. The plasma treated carriers also have improved wetting and exclusion of entrapped air in the carrier indentations. In some embodiments, the plasma treatment may comprise gas plasma treatment. The gas plasma treatment may impart surface chemistry through the introduction of oxygen, nitrogen, carbon dioxide, nitrous oxide, ammonia or combinations thereof. In some embodiments, the polystyrene films are plasma treated with two pure gases such as oxygen and ammonia, either sequentially, or as a gas mixture of oxygen and ammonia. The plasma treatment typically increases the oxygen content of the surface, introducing hydrophilic ketone, carboxylate and hydroxide moieties on the surface. The modified surface chemistry may help in adsorption of extracellular matrix proteins (ECM) such as fibronectin, fibrinogen, vitronectin, laminin, etc., which enhances cell attachment and cell proliferation on the treated surface.

One index of hydrophobicity or hydrophilicity is the contact angle of a water droplet on the surface. Contact angle can be measured by techniques well-known in the art. For example, a measurement of the water contact angle formed on a flat polystyrene film is proportional to the degree of hydrophilicity imparted by the plasma treatment. In one or more embodiments, the water contact angle for the plasma treated carrier surface may be in a range from about 10° to about 90°. In some embodiments, the water contact angle for the plasma treated carrier surface is from 30° to 70°. The water contact angle increases over time after plasma treatment due to surface chemistry reorganization to an equilibrium state. The plasma treatment further provides a surface chemistry with long-term stability.

In some embodiments, the plasma treatment may be carried out in a plasma reactor. The plasma reactor may be a vacuum vessel with a gas at low pressure, typically 10 to 1000 mTorr. When a high frequency electric field is generated in the reactor, plasma is formed containing reactive species like ions, free radicals and vacuum-UV photons. These species may react with the polymer surface and may cause chemical modifications accompanying with corresponding changes in various properties, which depend on the nature of the gas and the plasma parameters. Gases such as oxygen, ammonia and argon are typically used for modification of the polymer surfaces. In some embodiments, carbon dioxide, ammonia, nitrous oxide, or nitrogen is used for plasma treatment. In one embodiment, the polymer surface is modified by oxygen-plasma treatment to increase the cytophilicity of the surface. The surface functionality may also be altered via wet chemical methods such as oxidation treatments using perchloric acid or permanganate or partial hydrolysis using strong acids or bases.

In addition to gas type, the plasma system has different factors, such as process settings that can be varied. In one or more embodiments, the factors include chamber pressure, device power (50-2000 W), duration, gas flow rate and plasma mode. The chamber pressure, device power, duration and gas flow rate are continuous factors, which are maintained during the whole procedure. The plasma mode in some systems may be set to either reactive ion etch (RIE) or plasma etch (PE) mode, with the reactive ion etch mode as one of the desired modes in these embodiments.

In some embodiments, the surfaces are treated with corona discharge to modify one or more surface properties of the carriers. In corona discharge treatment, a current develops from an electrode with a high potential in a neutral gas, such as air. Ionization of the gas generates a layer of plasma around the electrode. The ions generated eventually pass the charge to nearby areas of lower potential, or recombine to form neutral gas molecules. Surfaces of organic films such as polystyrene, polyesters and others may be oxidized when exposed for a short time to the reactive air plasma generated by corona discharge. Corona discharge treatment can increase the oxygen content on the polymer surface and improve the film wettability by water.

Generally, mouse or human fibroblast feeder cell layers are used to support stem cell growth. Cell-free conditioned media are used substantially to prevent contamination. The use of chemically defined media without animal-derived components has been used for culturing iPSCs. The embodiments of the carriers may comprise a coating that provides a xeno-free alternative to feeder cell layers which reduces the probability of contamination. The present embodiments of the carriers provide feeder-free culture conditions, and in some embodiments chemically defined coatings, which are useful for culturing cells that may safely be used for therapeutic applications.

A variety of biomolecular coatings may be used to modify the carrier surfaces to enhance cell attachment. In some embodiments, the carriers further comprise biomolecular coatings, such as proteins or peptides on the plasma treated carriers. In these embodiments, the biomolecular coating is disposed on the plasma treated surface to further increase cytophilicity. In some other embodiments, the non-plasma treated carriers are coated with biomolecular coatings. In these embodiments, the biomolecular coatings are disposed directly on the carrier surface.

One or more embodiments of the carrier comprise biomolecular coatings that comprise biologically derived proteins or peptides, recombinant proteins or synthetic peptides. In one embodiment, the coating comprises extracellular matrix (ECM) proteins, proteoglycans, factors derived from a mouse sarcoma cell line or combinations thereof. In some embodiments, the biologically derived proteins may include various structural proteins such as collagen, laminin, entactin, vitronectin or fibronectin. In some embodiments, the coating comprises recombinant proteins. The recombinant proteins may include laminin 511 or laminin 521. In one embodiment, the surfaces are modified with recombinant vitronectin to enhance surface cytophilicity for better attachment of the cells. In some embodiments, cells are attached to extracellular matrix (ECM) through integrin, which is a cell adhesion receptor that supports cell proliferation and differentiation. Integrin can bind to ECM proteins, such as collagen, fibronectin, vitronectin, laminin and N-linked glycoproteins.

The coating may further comprise natural polypeptides or synthetic polypeptides. In one or more embodiments, the coating further comprises growth factors that promote differentiation or proliferation of induced pluripotent or multipotent cell types. The coated surfaces support adhesion and expansion of stem cells in their undifferentiated state or directed differentiation into specialized cell types. One or more embodiments of the coating may comprise growth factors such as bFGF, TGF β1, Human Insulin, Human Holo-Trasferrin, Human Serum Albumin, Glutathione or combinations thereof. In some embodiments, the synthetic peptide comprises the RGD sequence. Most of the ECM proteins include RGD peptide sequences and the cells can be attached through RGD binding via integrin to provide undifferentiated proliferation of hiPSCs in serum-free media.

The plasma treated carriers are compatible with coatings used for hiPSC, such as, Matrigel™, recombinant proteins such as Laminin521, or synthetic substrates such as Synthemax® II. In one embodiment, the coating comprises Matrigel™, which is used as an attachment substrate for culturing induced pluripotent stem cells. In the absence of feeder cells, the induced pluripotent stem cells are grown using Matrigel™, which comprises extracellular matrix components derived from a mouse sarcoma cell line (Engelbreth-Holm-Swarm) extracellular matrix material. The Matrigel™ is heterogeneous in composition containing different structural proteins including laminin, entactin and collagen with adhesive peptide sequences. Matrigel™ contains numerous other proteins in different amounts and its exact composition may vary. In another example, the coating material for culturing hiPSC may include Laminin521 or Synthemax® II.

The carrier surface may be modified, for example, to enhance cell release as well as cell attachment. The coating may be made, for example, of a thermoresponsive polymer, pH responsive polymer, or combination thereof. Thermoresponsive polymers may include, but are not limited to, poly (N-isopropylacrylamide) (PNIPAM), poly(di(ethyleneglycol)methylether methacrylate) (PDEGMA). pH responsive polymers may include, but are not limited to, copolymers of acrylic acid, dimethylaminoethylacrylate, and hydroxyethylacrylate. The coating may comprise one or more layers. In some embodiments, where the coating comprises multiple layers, the layers may be homogeneous or heterogeneous. For one example, one layer may be made of thermoresponsive polymer, and another layer may be made of pH responsive polymer. Thermoresponsive or pH responsive polymer coatings on the surface can facilitate easy release of cultured cells from the carrier surface.

The structured indentations may also form relief features on the carrier surface. The relief feature may be present on one or more surfaces of the carriers, which prevents the carriers from sticking to each other. Carrier sticking or clumping has been seen to be an issue with certain types of flat or smooth carriers during low shear mixing. The relief features on the carrier also serve to prevent the carriers from sticking to the inner walls of the reactor or culture vessel, which facilitates cleaning the reactors/culture vessels between batches of cell culture.

A cross sectional profile of each indentation may have, as non-limiting examples, a polygonal, a circular, or an elliptical shape. Each of the polygonal indentations may have, as non-limiting examples, a triangular, rectangular, square, pentagonal or hexagonal shape. The dimension of the major axis and minor axis of the indentations may be the same or different.

The carrier may be made of glass, polymer, ceramic, metal or a combination thereof. In one embodiment, the carrier is made of a polymer or a copolymer or a blend of polymers. The polymers may comprise, but are not limited to synthetic and natural polymers such as, polyester including polyethylene terephthalate (PET), polystyrene, polycarbonate, polyamide, polyurethane, olefin polymer, dextran, silicone, or polyacrylate, polymethacrylate or copolymer or blend of polymers thereof. In one specific embodiment, the carrier is made of polystyrene.

In one or more embodiments, the carrier is made of a material having a density between 1.0 and 1.4. The density of the material is a significant factor for efficient carrier suspension in a liquid media inside a bioreactor. The material, such as polystyrene provides a density to the carriers which enable the carriers to suspend efficiently in the liquid media and also protects the cells from shear. The inclusion of one or more density modifiers to the polystyrene may result in decreasing the density of the material. For example, entrapped air in the carrier or hollow microspheres present in the carrier may reduce the density of the carriers. The decrease in density may be beneficial for the carriers to efficiently suspend and mix in the liquid media and reduce the shear force on the cells.

The polymer may be transparent, which allows cell observation under an optical microscope. In certain embodiments, the carrier has a substantially planar disc shape, which facilitates cell visualization by preventing lensing effects. Refraction of light can be a hindrance to visualization of cells on spherical carriers of certain refractive index. Cell visualization is useful, for example, for culturing and monitoring cells during stem cell expansion. In some embodiments, the polymer and surface treatment is substantially free of components of animal origin. This is especially beneficial in therapeutic applications, e.g. in the production of cells for cellular therapies. The polymer may be rigid at room temperature or cell culture temperature, non-porous and may have non-swelling properties in water, PBS or growth medium. The rigid, non-swelling, non-porous properties of the polymer can facilitate cell release, for example, when using standard enzymatic release protocols.

An example of a method of making a carrier for growing cells, comprises providing a single or a plurality of flat films and laminating the flat films to form a solid support. The solid support is subjected, to a method such as embossing, casting thermoforming, or injection molding to form structured indentations. In some embodiments, the solid support is embossed to form an embossed solid support, and the embossed solid support is cut into a plurality of portions or pieces to form a plurality of carriers. The plurality of embossed carriers is further treated with plasma to form plasma treated embossed carriers. In some other embodiments, the solid support is embossed to form structured indentations and make an embossed solid support, which is further treated with a plasma to form a plasma treated embossed solid support, followed by cutting or dicing the plasma treated embossed solid support to a plurality of portions or pieces to form a plurality of carriers. In one example, the embossing of the solid support is performed using a mold.

Figure 3A:
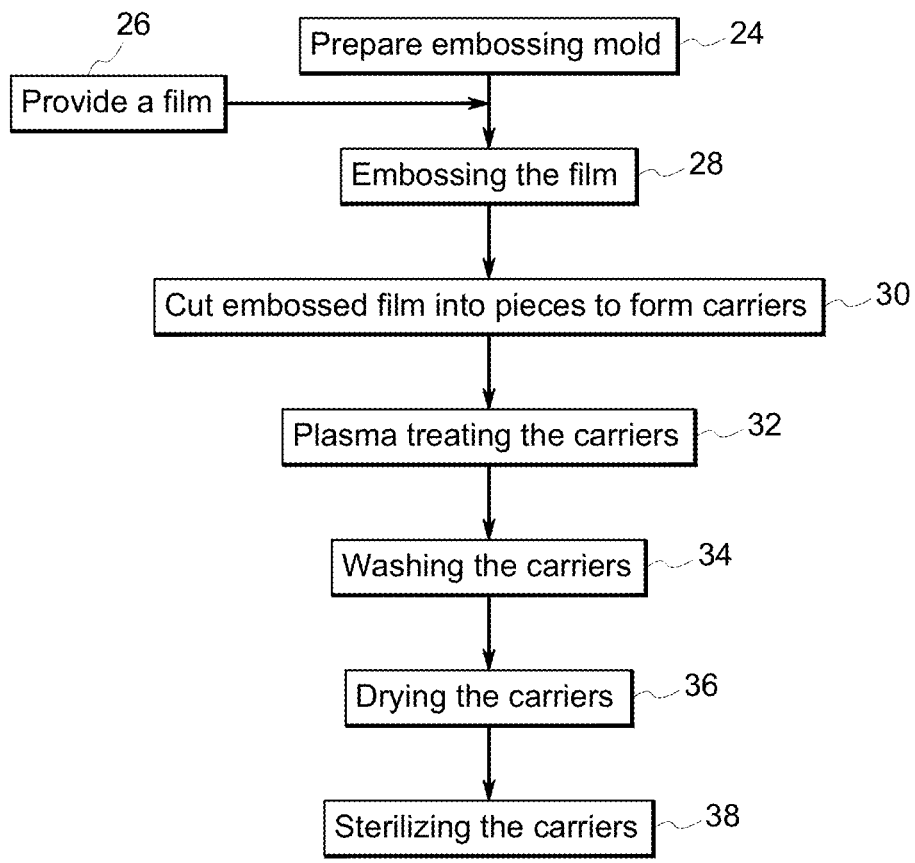
FIGS. 3A and 3B are process flow diagrams of alternative examples for methods of making carriers of the invention on a small scale in batch mode.
Figure 3B:
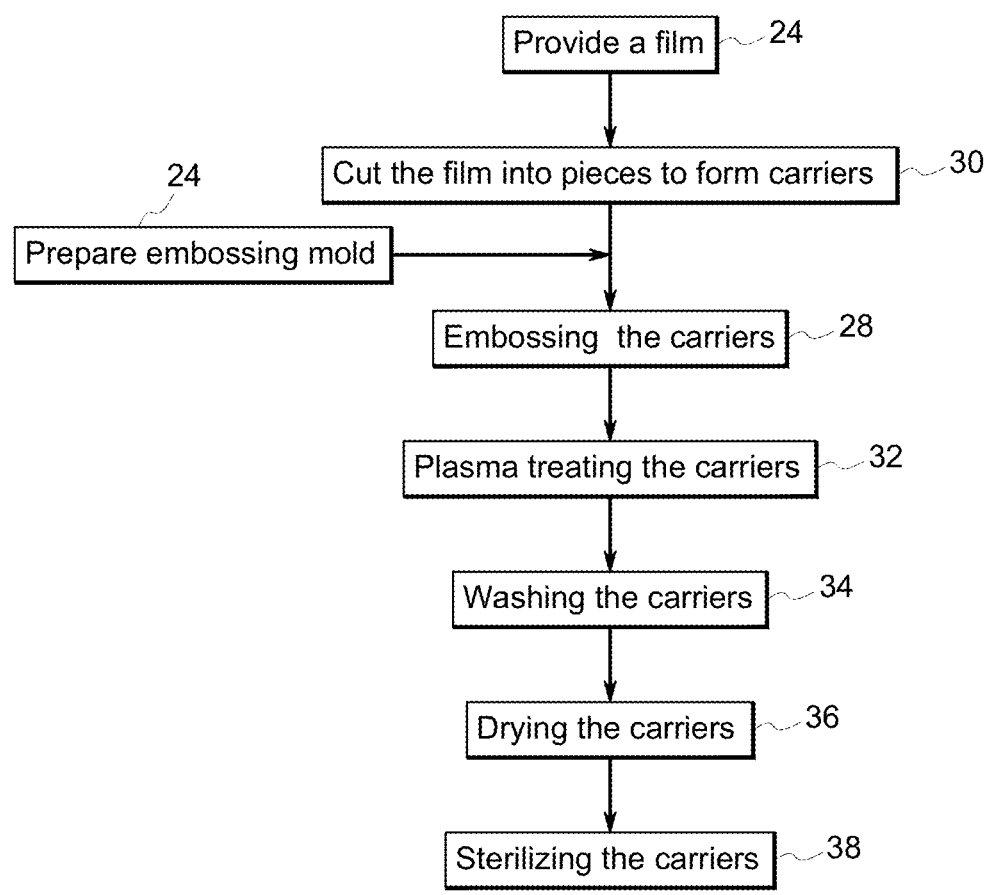

In one example, a process for making a carrier for growing cells is generally illustrated in flow diagrams of FIGS. 3A and 3B. The process comprises two alternate methods, method (1) as shown in FIG. 3A and method (2) as shown in FIG. 3B. The method (1) comprises the steps of preparing embossing mold 24, and providing a film from a roll 26, followed by embossing the film 28. The embossed film is then diced or otherwise discretized into a plurality of carriers 30 followed by treating with plasma 32 to form plasma treated embossed carriers. In some embodiments, the embossed film is optionally plasma treated on the other side of the film for better uniformity of treatment. The plasma treated embossed carriers are then washed 34 with a wash fluid such as water or a mixture of water and alcohol to remove fine particles. The washed carriers are then dried 36 before subject to sterilization. In some embodiments, the dried carriers are sterilized 40 using gamma sterilization.

The method (2) (FIG. 3B) also may comprise the steps of preparing embossed mold 24, providing a film 26 and cutting the film from a roll into pieces to form the carriers 30. The carriers are then embossed 28 using the embossing molds. In contrast to the method 1, wherein the embossed film is obtained from a source and then the film is processed to cut the films into small pieces, method 2 comprises the step of dicing or otherwise discretizing the film into a plurality of carriers 30 before embossing the carriers 28. The carriers are then subjected to a plasma treatment 32 in bulk accompanied by mixing to ensure uniformity of surface treatment to form plasma treated embossed carriers. The plasma treated carriers are then washed with a wash fluid such as water or a mixture of water and alcohol to remove fine particles 34, followed by drying 36. The methods (1) and (2) (as described above for FIGS. 3A and 3B respectively) can be modified to produce carriers on large scale using roll-to-roll operations for some or all of the steps of manufacturing. For example, the embossing or structure generation step can be scaled-up into a roll-to-roll operation, and the plasma treatment operation can be done in bulk in drum-style treaters, and the discretization can be done via roll-to-roll or sheet-fed cutting operations.

Figure 4A:
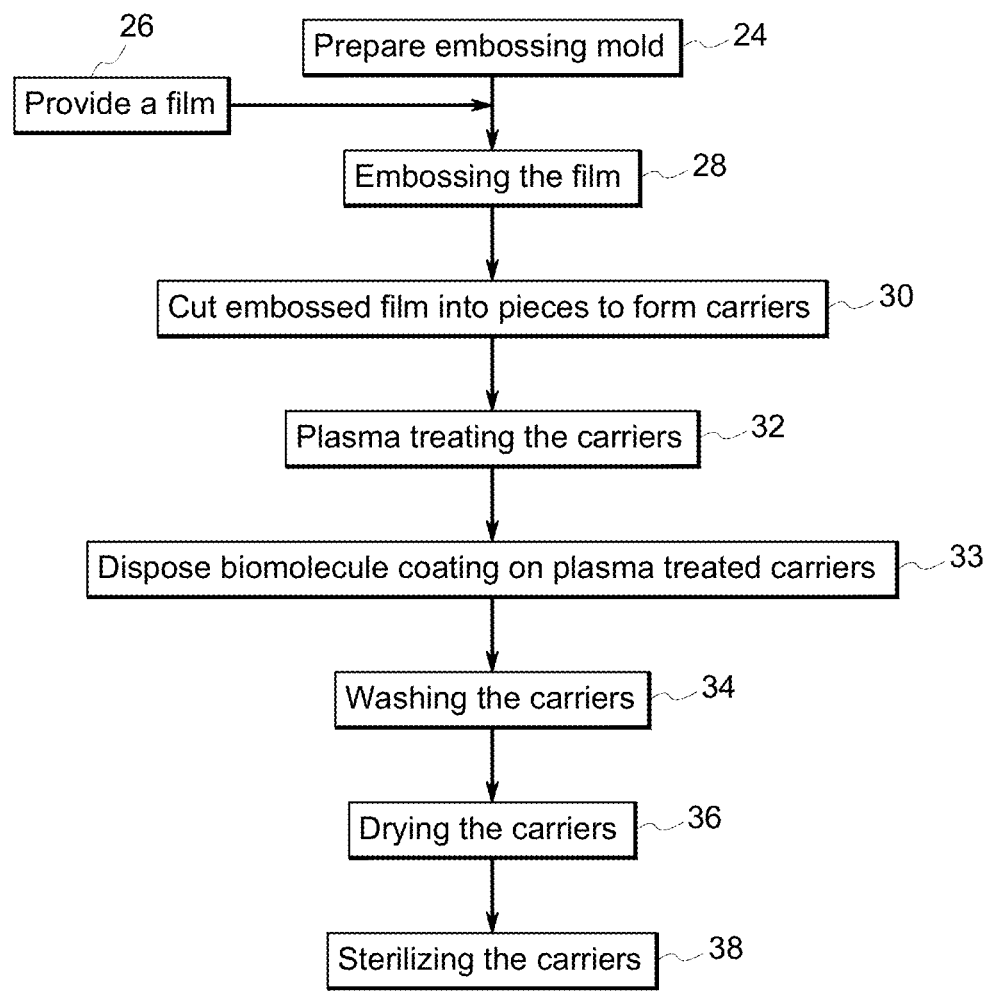
FIGS. 4A and 4B are process flow diagrams of alternative examples for methods of making carriers of the invention on a small scale in batch mode.
Figure 4B:
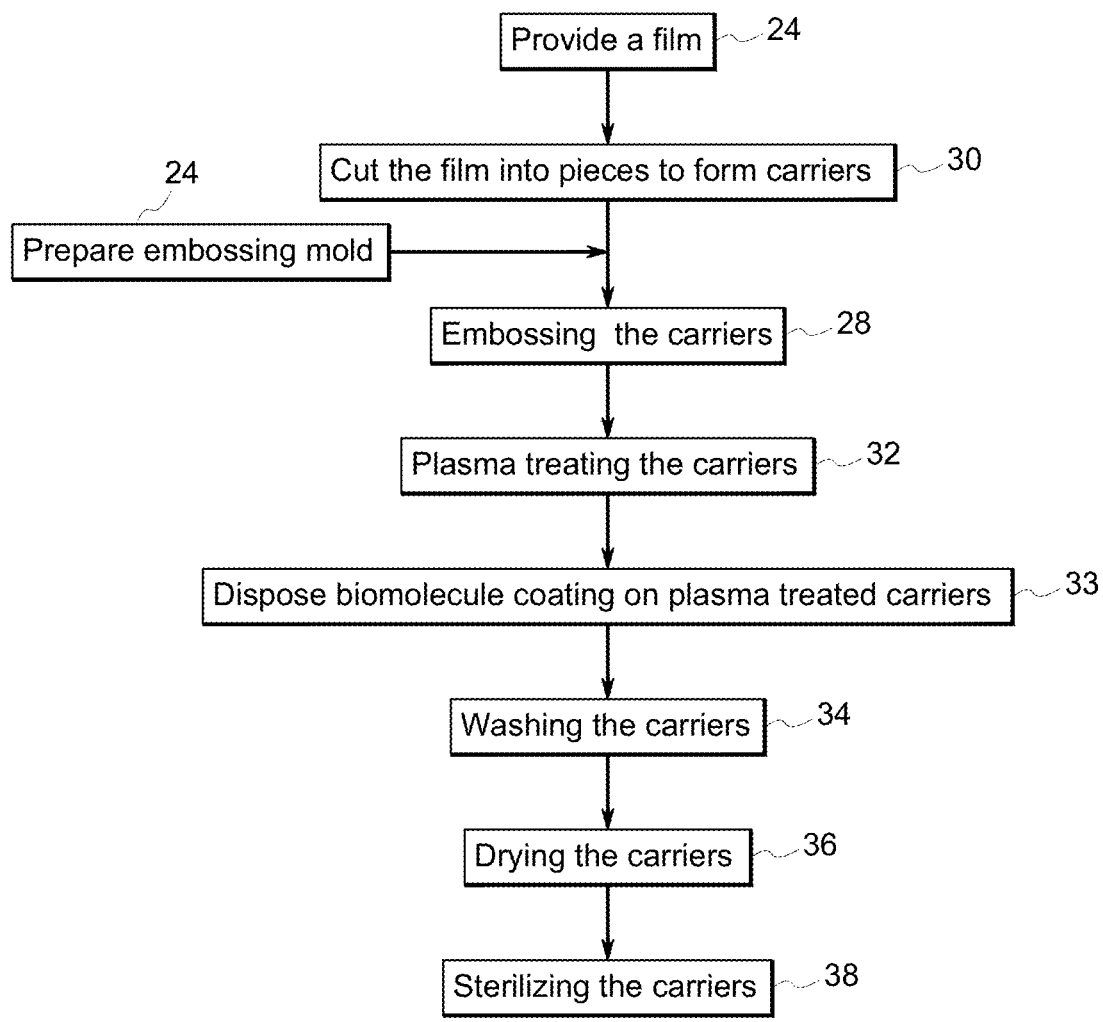

In one example, a process for making a coated carrier for growing cells is generally illustrated in FIGS. 4A and 4B. The process comprises two alternate methods, method (1) (FIG. 4A) and method (2) (FIG. 4B). The method (1) of FIG. 4A comprises the steps of preparing embossing mold 24, and providing a film from a roll 26, followed by embossing the film 28. In some embodiments, the embossed film is obtained from a source and then the film is processed to cut the film into plurality of portions or pieces to form a plurality of embossed carriers 30. In some embodiments, the plurality of embossed carriers further treated with plasma 32 to form plasma treated embossed solid support/carriers. In some embodiments, the embossed carriers are optionally plasma treated on the other side of the carriers for better uniformity of treatment 32. In some embodiments, a biomolecular coating is disposed 33 on the plasma treated carriers.

The method (2) of FIG. 4B also may comprise a method comprising the steps of providing a film 26, the film is cut or diced or otherwise discretized to generate pieces to form carriers 30, which can then be sieved to a narrow size distribution. An embossed mold 24 is prepared followed by embossing the carriers 28. In some embodiments, the carriers are optionally washed with a wash fluid such as water or a mixture of water and isopropyl and/or ethyl alcohol to remove fine particles, followed by drying. In some other embodiments, the carriers are then subjected to a plasma treatment 32 in bulk accompanied by mixing to ensure uniformity of surface treatment to form plasma treated embossed carriers. The plasma treated carriers are then washed with a wash fluid such as water or a mixture of water and isopropyl and/or ethyl alcohol to remove fine particles. In some embodiments, a biomolecular coating is disposed 33 on the plasma treated and washed carriers. In some other embodiments, the biomolecular coating is directly disposed on the non-plasma treated carriers. The plasma treated carriers are then washed 34 with a wash fluid such as water or a mixture of water and isopropyl alcohol to remove fine particles followed by drying 36. The methods (1) and (2) (as described above, FIGS. 4A and 4B) can be modified to produce carriers on large scale using roll-to-roll operations for some or all of the steps of manufacturing. For example, the embossing or structure generation step can be scaled-up into a roll-to-roll operation, and the plasma treatment operation can be done in bulk in drum-style plasma reactors, and the discretization can be done via roll-to-roll or sheet-fed cutting operations. The coated and plasma treated carriers are then sterilized 40 before use in the laboratory.

Another example of a method for making the carriers comprises initially providing two flat polymer films. The method further comprises forming one or more structured indentations on the two flat polymer films individually on at least one surface of each of the two films, such as by embossing to make two embossed polymer films (embossed on one side each), and laminating the two embossed polymer films together, back to back, to form a composite laminated embossed polymer film, so that the outwardly facing surfaces comprise one or more of the structured indentations. The laminated embossed polymer film may then be diced to form a plurality of untreated carriers. The untreated carriers are then treated with a plasma treatment to form a plurality of plasma treated carriers. To create structured indentations, the flat polymer films may alternatively be subjected to casting thermoforming, or injection molding, or a bulk polymer may be made into a solution and cast on a mold to form a film with the structured indentations. In another embodiment, a method comprises initially providing two polymer films with embossed structure on one side (surface) of the film. These two films are provided, laminating the two embossed polymer films together, back to back, to form a composite laminated embossed polymer film, so that the outwardly facing surfaces comprise one or more of the structured indentations.

The structured indentations may be formed in the carrier by one or more of the following methods. In one example, a textured roll is used to make the structured indentations on a heated polymer film in a roll-to-roll process. In another example, a flat mold is prepared by cutting or machining the negative of the desired indentations into a metal block. The metal block then may be used as-is or replicated first as a positive and then as a negative, using, for example, a polymer casting process. The negative mold can then be used in a batch-stamping or hot embossing process to emboss the pattern into a polymer film. In another example, a mold thus formed can be used in a solvent-casting process to make the polymer film with the structured indentations. A polymer solution can be coated on to the mold or textured roll, and dried and/or cured. The dried/cured film then peeled off to yield a film with the desired structured indentations. Alternate methods such as thermoforming or injection molding may also be used.

A cell culture system of the invention uses one or more of the carriers for growing cells. In one embodiment, the cell culture system is a bioreactor, more specifically, an agitated bioreactor. As mentioned herein, a bioreactor may refer to any device or system that supports cell growth. In one aspect, a bioreactor may refer to a device or a system for growing cells or tissues in the context of cell culture or tissue engineering. The bioreactor may employ agitation, generated by an internal impeller or paddle, or via externally rocking, rolling or shaking the culture vessel, or via bellows-induced motion of fluid. The bioreactor may, for example, be a reactor with rocking or rolling motion, such as Wave and Xuri Bioreactors™, a stirred tank bioreactor, such as an Xcellerex® bioreactor, a fluidized bed bioreactor, fixed bed bioreactor, a roller bottle or airlift bioreactor or a perfusion bioreactor.

The Xuri and Wave Bioreactors™ comprise a rocking platform supporting a vessel containing a culture fluid, wherein the culture fluid comprises cells in a culture media. The rocking motion of the platform induces mixing and mass transport in the culture fluid. A stirred tank bioreactor generally comprises an impeller system and optionally a sparging system to mix and aerate the culture. An airlift reactor relies on rising gas bubbles to mix and aerate the culture medium. Hydrodynamic factors such as mass transfer, mixing efficiency, and shear stress experienced by cells can be different in the different types of bioreactors. In addition, the cell growth rate and quality of cells may be influenced by operational differences between reactor types.

In another embodiment, the bioreactor may be a stirred tank bioreactor which, under operational condition, comprises a vessel containing the cell growth medium, cells, and carriers. The carriers are agitated through the use of a mechanically or magnetically actuated paddle, screw, impeller or other rotational device (or devices) for mixing the contents of the reactor. Specifically, it is beneficial to ensure that the impeller is raised to a sufficient height above the bottom of the reactor that it does not directly impinge on the bed of carriers. The arrangement of impellers which are raised to a sufficient height above the bottom of the reactor provides two benefits, first, it prevents cells on the carriers from interacting directly with the impeller and generating high local shear and second, it prevents the carriers from becoming bound between the impeller and the vessel walls which may cause high local shear, carrier breakage and hindered proper mixing of the media. Finally, as opposed to traditional bioreactor growth, where shear is not as great of an issue, intermittent, low rate stirring is beneficial in these embodiments as it limits the total amount of potential shear stress of the cells. In one or more embodiments, the bioreactor may be a perfusion bioreactor.

The Corning disposable spinner flask is a stirred tank reactor that consists of a 125 mL or 500 mL reservoir, an impeller (paddle) and integrated magnet. The unit comes presterilized, eliminating the need for time-consuming assembly or cleaning and reassembly. The paddle size and height may be optimized for different vessel size or volume and to prevent wedging carriers between the impeller and the bioreactor housing. The spinner flasks sit on a magnetic stirrer that controls the stir rate and provides smooth and even rotation of the impeller. Thus, the hydrodynamic factors including fluidization of the carriers and shear stress can be controlled.

An example of a method of culturing induced pluripotent stem cells comprises providing one or more carriers for growing cells in a bioreactor, adding culture medium, adding an inoculum of cells to the carriers, allowing attachment of cells to the carriers, suspending the carriers in the medium continuously or intermittently, and allowing the cells to grow on the carriers. Cells may be grown in a culture flask or plate prior to addition to the carriers. In some other embodiments, the carriers may be introduced into a spinner flask, a stacked culture flask, a stirred tank reactor, a Xuri or Wave Bioreactor™ or any other in-vitro cell culture system.

Cultured cells may be detached or released from the carriers by a variety of methods. The cells may be released, for example, by using a mechanical method, adding an enzyme, changing environmental stimuli, such as changing temperature for a thermoresponsive polymer coated or based carriers or changing pH for a pH responsive polymer coated carriers or a combination thereof. The cell release by mechanical method includes cell scraping. The cells may also be released by treating with proteolytic enzymes, such as accutase or trypsin. One non-enzymatic method uses calcium chelators, such as EDTA. Other non-enzymatic methods include, but are not limited to, physical methods that use ultrasound, which generates bubbles that facilitate cell detachment. Cultured cells from carriers comprising thermoresponsive polymers, such as poly-N-isopropylacrylamide (PNIPAAm) may be released by cooling the carrier to a temperature below the lower critical solution temperature (LCST).

In one or more embodiments, the cells are passaged repeatedly. Cell passaging refers to cell splitting, a technique which keeps the cells alive and allows the cells to expand under culture conditions for extended periods of time. Typically cells are passaged when the cells are greater than 70% confluent, but could be passaged at a lower cell density. As used herein, the term "passage" encompasses a complete cycle of cell seeding on the carriers, cell culturing on the carriers and releasing the cells from the carriers. During cell culture, the old media is replaced after every one or two days by a new media that enables the cells to grow for a longer period of time. In some embodiments, the cells are seeded on the carriers, cultured on the carriers and released from the carriers and the cycle is repeated for more than one time. In these embodiments, the released cells are further seeded on unused (new) carriers followed by culturing and releasing the cells. In some other embodiments, the cells are passaged repeatedly, wherein the released cells are further seeded on the used carriers. In some other embodiments, the cells are passaged repeatedly using used and unused carriers both.

The carriers can be used in combination with a bioreactor or culture vessel, to provide or enhance surface area for the attachment and growth of anchorage-dependent cells. Some embodiments of the kit of the invention for culturing cells comprise a disposable housing or vessel pre-loaded with one or more carriers. In one embodiment, the carriers and the disposable housing or vessel may be provided separately. In one embodiment, the housing may be reusable. The housing may be, for example, a bag, a flask, a tank, a tube, a petri dish or a bottle. The kit may further comprise culture media suitable for cell growth. The kit may comprise cells in a frozen condition and may further comprise a protocol for using the carriers.

The present embodiments provide culture and release of induced pluripotent cells with high purity, high efficiency and high yield from the plasma treated engineered surface, such as an embossed surface that may protect the adherent, shear-sensitive cells, such as human induced pluripotent stem cells. In one or more embodiments, human induced pluripotent stem cells are seeded onto the polystyrene carriers, which protect the cells from fluid induced shear that may result in cell death and differentiation, specifically when the cells are cultured in a bioreactor. In the absence of shear forces, the hiPSCs may be able to grow and expand maintaining the pluripotency. In one or more embodiments, the carriers are easily separable from the cultured hiPSCs. The density of the carriers may be slightly higher than the density of the growth medium.

Induced pluripotent stem cells (iPSC) are generally derived from adult tissues and the cells are a type of pluripotent stem cells. iPSCs were first reported in 2006 by Shinya Yamanaka (Kyoto University, Japan) and human iPSCs that express stem cell markers and are capable of generating cells characteristic of all three germ layers (endoderm, mesoderm and ectoderm) were first reported in late 2007. iPSCs are typically derived by introducing pluripotency associated genes, also known as "reprogramming factors" into a given cell type, such that the iPSCs achieve an embryonic stem cell-like state.

Since iPSCs can be derived directly from adult tissues, their development can bypass the requirement for embryos. Moreover, iPSCs can be made from patient specific sources (i.e., autologous cells) which minimize the risk of immune rejection. iPSC offer a novel cell source for regenerative medicine, toxicological screening and in vitro modelling of genetic disorders. The expansion of induced pluripotent stem cells greatly facilitates various applications, such as, transplantation, tissue engineering, etc. using autologous or allogenic cell sources. Sufficient expansion and recovery of adult stem cells may overcome the limitations of using adult stem cells for various applications. The sufficient expansion and subsequent differentiation of adult-derived pluripotent stem cells such as induced pluripotent stem cells may replace embryonic stem cells for various applications.

EXAMPLE 1

Fabrication of Carrier for Growing Cells

Figure 5A:
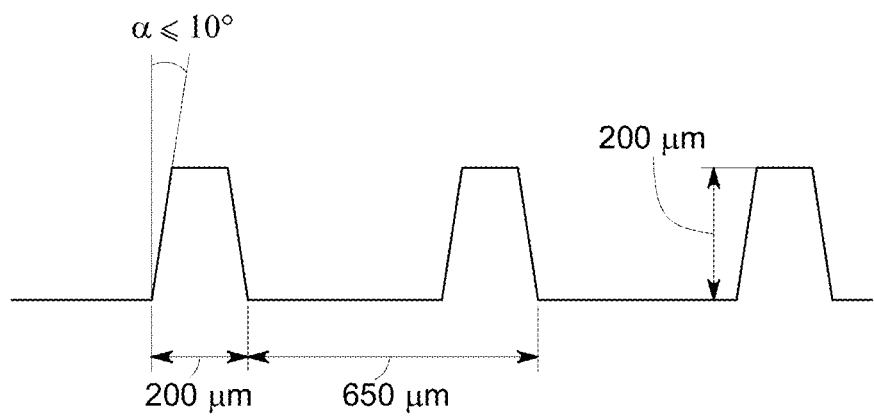
FIGS. 5A and 5B are schematic representations of the embossed pattern used for embossing the carriers on one side and on two-sided "waffle" morphology, respectively.
Figure 5B:
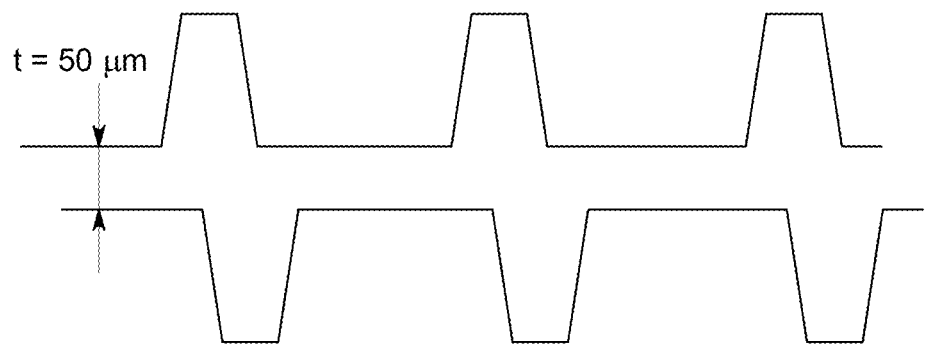

Method of making embossed carriers—Multiple sheets of biaxially oriented polystyrene film (Trycite 1003U, Dow Chemical Company) were placed in between two molds or pattern as shown in the schematic in FIGS. 5A and 5B with patterns facing in. The number of sheets or film was chosen so that the volume of polystyrene was sufficient to fill the pattern in the molds and still leave a small amount of polystyrene separating the molds. The films were then embossed (28, FIG. 3A) in a heated hydraulic press with 1000 lb force and a temperature cycle that ramped up to 150° C. for 5 minutes and then cooled to below 60° C. The embossing process fused the multiple sheets of film into a single monolithic structure that replicated the texture of the molds and pattern-master on both sides. The embossed polystyrene film was removed from the molds after cooling to room temperature.

Dicing of the film to generate carriers—Carriers for cell culture were prepared from the embossed sheets either by manually cutting the film into 6.5 mm×6.5 mm pieces or 2 mm×2 mm pieces, or by discretizing and then sieving to select a particular size range, or by punching circular or hexagonal discs of the desired size. The embossed film was cut into hexagonal macrocarriers depicted in the schematic as shown in FIG. 6A.

EXAMPLE 2

Preparation of Plasma Treated Carriers

To make the carriers compatible for cell growth, the carriers were $O_2$ plasma treated (32, FIG. 3A). Carriers were embossed on both sides with 650 nm pitch waffle pattern (450 nm square well size with a depth of 200 µm) and cut into hexagonal pieces (0.25" edge-to-edge width). 1135 g carriers were plasma treated in each batch. The embossed carriers were plasma treated in a custom-made rotating drum plasma system with a central rod anode, at 25° C. The plasma was generated at 500 W with a 1000 sccm flow of $O_2$ for 18 minutes with a rotation rate of about 5 rpm. The plasma treated carriers were stored at room temperature and ambient humidity for approximately one month before aliquots were prepared (1.17 g/batch) in polypropylene 50 mL centrifuge tubes. Each aliquot was washed thrice with isopropanol, four times with 18.2 MΩ deionized water and thrice with 70% Ethanol/$H_2O$ (vol/vol.).

Batch Washing of the plasma treated carriers—Carriers were washed using ethanol/water ($H_2O$). 300 g of carriers per batch were washed with 70% Ethanol/$H_2O$ for at least 3 times. The carriers were agitated in the wash solution, drained and dried centrifugally thrice, prior to overnight drying in a vacuum oven (40° C., 5 Torr) for at least 4 hours.

Sterilization—The carriers were heat sealed in a low density polyethylene (LDPE) bag and subjected to gamma sterilization (25 kGy). After gamma sterilization, the carriers were ready to use for cell culture. Cell carriers of different designs were made using the above fabrication procedures. The embossed cell carriers of the invention may include carriers with alternate wall shape made by using the embossed pattern as shown in FIG. 5A (one side), and FIG. 5B (two-sided). One embodiment of the embossed one sided pattern of FIG. 5A shows specific dimensions including each well width (450 µm), the width (200 µm) and length (200 µm) of each wall of the well. One embodiment of the embossed two-sided "waffle" pattern of FIG. 5B shows specific dimension, such as width (t) (50 µm) of the carrier.

EXAMPLE 3

Preparation of Matrigel™ Coated Carriers

The plasma treated carriers (from Example 2) were transferred under sterile conditions to a Corning 125 mL disposable spinner flask (#3152). The Ethanol/Water sterilization solution was pipetted off and the carriers were washed twice with PBS. The carriers were then coated with 7 mL of BD Matrigel™ diluted 1:20 in DMEM/F12 for 60 minutes with mixing every 20 minutes, followed by 0 or 1 wash with PBS.

EXAMPLE 4

Materials and Reagents Used for Cell Culture on the Carrier and Subsequent Cell Release Materials: The materials used for the subsequent examples include centrifuge tubes, disposable spinner flasks purchased from Corning® (MA, USA). Matrigel™ matrix was purchased from BD Biosciences. Accutase™ was purchased from MP Biomedical (CA, USA) and Invitrogen™ (NY, USA); TrypLE was purchased from Invitrogen (NY, USA). TeSR™-E8 medium was purchased from STEM-CELL™ Technology Inc. (Vancouver, BC, Canada). Y-27632 (ROCK Inhibitor) was purchased from Sigma Aldrich (St. Louis, Mo.) and Millipore®.

Cell Carriers—The carriers used for the following examples had a length and width of 6.5 mm, and a height of about 0.5 mm The carriers comprised a plurality of structured indentations on each of the two outer surfaces. Each of the structured indentations had a major axis and minor axis of 0.45 mm each and a depth of 0.2 mm The carriers used for the majority of experiments using hiPSC were 6.5 mm hexagonal carrier with height of 50 micron. A schematic drawing of hexagonal embossed carrier with specific dimension used for culturing cells is shown in FIG. 6A. FIG. 6B shows a cross sectional view of a carrier and FIG. 6C is a magnified view of the cross sectional side view of the carrier with specific dimension.

Cells: NL5 (also known as NCRM-5) and NC-1 cell lines (human induced pluripotent stem cells) were obtained from Guokai Chen at the National Heart, Lung, and Blood Institute iPSC and Genome Engineering Core Facility.

EXAMPLE 5

Seeding and Expansion of NL-5 and NC-1 Induced Pluripotent Stem Cells at 100 cm²-scale The human induced stem cell lines (iPSC) NL-5 (also called NCRM5), and NC-1 were grown on Matrigel™ coated 6-well tissue culture polystyrene plates prior to this experiment. Cells were washed once with phosphate buffered saline (PBS) and treated with Accutase™ for three minutes at 37° C. Cells were centrifuged at 200 G for 5 minutes and resuspended in TeSR-E8 medium. Cells were counted on a NucleoCounter NC-100 (Chemometec, Denmark).

The cells were seeded onto the Matrigel™-coated carriers in the spinner flask at a concentration of $1.8 \times 10^6$ cells/100 cm² on the projected surface area (1.17 g aliquot) in 50 ml TeSR™-E8™ with 10 µM Y-27632 (ROCK Inhibitor). The cells were seeded by intermittent stirring for 1 min at 78 rpm followed by 1 min static for 1 hour, followed by 18 h static culture. The next day, cells were maintained by intermittent stirring (1 minute on/45 minutes off) at 40 rpm until the time of harvesting (day 3 or day 4). Each day, half of the media was removed and replaced with fresh TeSR™-E8™. After 3 or 4 days, the cells were harvested from the spinner flasks. First, the media was removed, followed by a PBS wash, followed by the addition of 7 mL of Accutase™ which was gently stirred and returned to the incubator for five minutes. The suspended cells were removed and the carriers were washed with PBS to remove the remaining cells. The cells were then centrifuged at 200 G for 5 minutes and re-suspended in TeSR™-E8™ for counting via Nucleocounter. $12.4 \times 10^6$ live NL-5 cells were recovered for a fold expansion of 4.94 with a viability of 88% after 3 days in culture. $6.83 \times 10^6$ viable NC-1 cells were recovered for a fold expansion of 3.41 over 3 days and at a viability of 83%.

EXAMPLE 6

Serial Passaging for NL-5 Induced Pluripotent Stem Cells at 100 cm² Scale

NL-5 induced pluripotent stem cells were cultured on Matrigel™ coated 6-well plates prior to this experiment. Cells were washed once with phosphate buffered saline (PBS) and treated with Accutase™ for three minutes at 37° C. Cells were centrifuged at 200 G for 5 minutes and re-suspended in TeSR-8 medium. Cells were counted on a NucleoCounter NC-100 (Chemometec, Denmark).

The cells were seeded onto the Matrigel™-coated carriers in the spinner flask at a concentration of $1.5 \times 10^6$ cells/100 cm² projected surface area (1.17 g aliquot) in 50 ml TeSR™-E8™ with 10 µM Y-27632 (ROCK Inhibitor). The cells were seeded by intermittent stirring for 1 min at 90 rpm followed by 1 min static for 1 hour, followed by 18 h static culture. The next day, cells were maintained by intermittent stirring (1 minute on/45 minutes off) at 40 rpm until the time of harvesting (day 3 or day 4). Each day, half of the media was removed and replaced with fresh TeSR™-E8™. After 3 or 4 days, the cells were harvested from the spinner flasks. First, the media was removed, followed by a PBS wash, followed by the addition of 7 mL of Accutase™ which was gently stirred and returned to the incubator for five minutes. The suspended cells were removed and the carriers were washed with PBS to remove the remaining cells. The cells were then centrifuged at 200 G for 5 minutes and re-suspended in TeSR™-E8™ for counting via Nucleocounter. The cells were cultured on the carriers up to 5 passages and the expansion rates are shown in table 1 below. Cells were harvested on either day 3 or day 4 after seeding.

The fold expansion at each passage of a representative experiment is shown in FIG. 7. Consistent expansion rates were observed using the carriers throughout the 5 passage experiment, demonstrating the ability of the carriers to repeatedly detach and separate from the cells, allow re-seeding onto new or old carriers and expansion in spinner flasks. Table 1 shows the average fold expansion at 100 cm² scale among all serial passaging experiments, with an average of 4.8-fold expansion over 3 days and 7.4-fold expansion over 4 days.

TABLE 1

Average fold expansion and viability of NL-5 induced pluripotent stem cells over several passages at 100 cm² scale

| Days in culture | Fold expansion (average) | Viability (average) (%) |
| --- | --- | --- |
| 3 days | 4.8-fold expansion +/− 1.2 (5 data points) | 85.7% |
| 4 days | 7.4-fold expansion +/− 1.7 (7 data points) | 86.7% |

EXAMPLE 7

Confirmation of Pluripotency after 5 Serial Passages of Human Induced Pluripotent Stem Cells NL5 cells were maintained on carriers in stirred tank reactors for 5 serial passages, then analyzed for Oct4 and Tra-1-60 expression by flow cytometry, and karyotyping was done. Cells expanded on the carriers in spinner flasks demonstrated normal karyotype as determined by cytogenetic analysis on 20 G-banded metaphase cells, with all 20 showing no abnormalities. NL5 cells were fixed in 4% paraformaldehyde and permeabilized in 0.1% Triton X-100, then analyzed by flow cytometry using an Oct4 antibody (Cell Signaling Technology, Danvers, Mass.) conjugated with AlexaFluor 647 and Tra-1-60 antibody (Stemgent, Cambridge, Mass.) conjugated with R-Phycoerythrin (PE). Results are shown in FIGS. 8A to 8D show a flow cytometric evaluation of the pluripotency markers Oct4 and Tra-1-60 on NL5 cells serially passaged on the carriers of the invention in stirred tank reactors over 5 passages. FIG. 8A shows the axis for Oct4 and Tra-1-60, FIG. 8B shows forward scatter and side scatter properties of the cells, FIG. 8C is a negative control with isotype antibodies, FIG. 8D shows Oct4 and Tra-1-60 expression on NL5 cells serially passaged on the carriers of the invention in stirred tank reactors over 5 passages. The data demonstrate maintenance of pluripotency over 5 serial passages on the carriers of the invention in spinner flasks.

EXAMPLE 8

Seeding and Expansion of NL-5 Induced Pluripotent Stem Cells at 500 cm$^2$-Scale NL-5 induced pluripotent stem cells were cultured on Matrigel™ coated 6-well plates prior to this experiment. 7.5×10^6 NL-5 cells were seeded onto 500 cm$^2$ carriers in a 125 ml spinner with modified impeller. Seven inches of the impeller shaft was removed, effectively raising the impeller to improve suspension of the carriers in the cell growth medium and to avoid grinding carriers between the impeller and the bottom of the bioreactor when initiating stirring. Cells were seeded in 100 ml TeSR-E8 media with 10 µM ROCK inhibitor.

NL-5 cells were seeded by intermittent stirring for 1 min on at 90 rpm/1 min off for 1 hour, followed by 18 h static culture. The next day, cells were maintained by intermittent stirring (1 minute on/45 minutes off) at 40 rpm until the time of harvesting (day 3 or day 4). Each day, half of the media was removed and replaced with fresh TeSR™-E8™. After 3 or 4 days, the cells were harvested from the spinner flasks. First, the media was removed, followed by a PBS wash, followed by the addition of 35 mL of Accutase™ which was gently stirred and returned to the incubator for five minutes. After the accutase™ treatment, the bottom of the spinner flask was repeatedly struck with an open palm to aid in the release of cells from carriers and the suspended cells. 100 mL of PBS (without Ca$^{2+}$ or Mg$^{2+}$) was added and the carriers were stirred again at 90 rpm for 5 minutes in the incubator. After the five minute stir, the bottom of the spinner flask was again repeatedly struck with an open palm. The suspended cells were removed and the carriers were washed with an additional 25 mL of PBS, striking the bottom of the flask and pipetting gently to remove the remaining cells. The cells were then centrifuged at 200 G for 5 minutes and re-suspended in TeSR™-E8™ for counting via Nucleocounter. Results from three independent experiments showing iPSC expansion after 3 or 4 days in culture on carriers at 500 cm$^2$ scale is shown in FIG. 9. The average fold expansion was 4.3-fold with 84% viability. The data demonstrates the ability of the carriers for seeding, expanding and harvesting iPSC in spinner flasks at a larger scale.

EXAMPLE 9

Serial Passaging of NL-5 Induced Pluripotent Stem Cells at 500 cm$^2$-Scale

NL-5 cells were cultured in static conditions as described above. 7.5×10^6 NL-5 cells were seeded onto 500 cm$^2$ carriers in a 125 ml spinner with modified impeller. Seven inches of the impeller shaft was removed, effectively raising the impeller to improve fluidization of the carriers and to avoid grinding through the settled carriers when initiating stirring. Cells were seeded in 100 ml TeSR-E8 media with 10 µM ROCK inhibitor.

NL-5 cells were seeded by intermittent stirring for 1 min on at 90 rpm/1 min off for 1 hour, followed by 18 h static culture. The next day, cells were maintained by intermittent stirring (1 minute on/45 minutes off) at 40 rpm until the time of harvesting (day 3 or day 4). Each day, half of the media was removed and replaced with fresh TeSR™-E8™. After 3 or 4 days, the cells were harvested from the spinner flasks. First, the media was removed, followed by a PBS wash, followed by the addition of 35 mL of Accutase™ which was gently stirred and returned to the incubator for five minutes. After the accutase™ treatment, the bottom of the spinner flask was repeatedly struck with an open palm to aid in the release of cells from carriers and the suspended cells. 100 mL of PBS (without Ca$^{2+}$ or Mg$^{2+}$) was added and the carriers were stirred again at 90 rpm for 5 minutes in the incubator. After the five minute stir, the bottom of the spinner flask was again repeatedly struck with an open palm. The suspended cells were removed and the carriers were washed with an additional 25 mL of PBS, striking the bottom of the flask and pipetting gently to remove the remaining cells. The cells were then centrifuged at 200 G for 5 minutes and re-suspended in TeSR™-E8™ for counting via Nucleocounter. During the serial passage experiment, cell culture maintained for 3 days expanded 2.9-fold with 93% viability, while the cell culture maintained for 4 days expanded 5-fold with 87% viability.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A carrier for expansion of induced pluripotent stem cells, wherein the carrier is configured for suspension in a bioreactor, and for protecting the cells from exposure to hydrodynamic shear generated by fluid motion in the bioreactor, comprising:
  a substrate comprising two outer surfaces, wherein one or more structured indentations are present on the two outer surfaces;
  wherein the two outer surfaces are modified with gas plasma treatment, the carrier has a length of about 6.5 mm, a width of about 6.5 mm, and a height of about 0.5 mm and each of the structured indentations has a major axis of about 0.45 mm, a minor axis of about 0.45 mm and a depth of about 0.2 mm.

2. The carrier of claim 1, wherein the gas plasma treatment comprises plasma treatment with one or more of the gases comprising oxygen, nitrogen, ammonia, carbon dioxide, nitrous oxide or combinations thereof.

3. The carrier of claim 1, wherein the gas plasma treatment comprises oxygen plasma treatment.

4. The carrier of claim 1, wherein the gas plasma treated carrier comprises a water contact angle between 10 and 70 degrees.

5. The carrier of claim 1, further comprising a biomolecular coating disposed on the two outer surfaces.

6. The carrier of claim 5, wherein the biomolecular coating comprises proteins or peptides.

7. The carrier of claim 5, wherein the biomolecular coating comprises proteins.

8. The carrier of claim 7, wherein the proteins comprise collagen, vitronectin, fibronectin, laminin, e-cadherin, recombinant laminin, recombinant collagen, recombinant vitronectin, recombinant e-cadherin or combinations thereof.

9. The carrier of claim 5, wherein the biomolecular coating comprises synthetic peptides.

10. The carrier of claim 5, wherein the biomolecular coating comprises extracellular matrix (ECM) proteins, proteoglycans, factors derived from a mouse sarcoma cell line or combinations thereof.

11. The carrier of claim 5, wherein the biomolecular coating forms a cytophilic surface.

12. The carrier of claim 1, wherein each of the structured indentations has a cross sectional profile of polygonal, circular, or elliptical shape.

13. The carrier of claim 1, wherein the carrier is made of a glass, polymer, ceramic, metal or combination thereof.

14. The carrier of claim 1, wherein the carrier is made of dextran, silicone, polyester, polycarbonate, polyamide, polyurethane, olefin polymer, or polyacrylate polymer.

15. The carrier of claim 1, wherein the carrier is made of polystyrene.

16. The carrier of claim 1, wherein the carrier is made of a material having a density between 1.0 and 1.4.

17. The carrier of claim 1, having a perimeter that is triangular, rectangular, square, pentagonal, hexagonal, circular, or elliptical.

18. A cell culture system comprising one or more of the carriers of claim 1.

19. The cell culture system of claim 18, wherein the cell culture system is a bioreactor.

20. The cell culture system of claim 19, wherein the bioreactor comprises fluid having a forced convective fluid motion.

21. The cell culture system of claim 20, wherein the bioreactor is a stirred tank bioreactor, or a reactor with rocking or rolling motion.

22. A kit for culturing cells, comprising a disposable housing pre-loaded with the carrier of claim 1.

23. The kit of claim 22, wherein the disposable housing comprises a bag, a flask, a tube, a petri dish, or a bottle.

24. A carrier for expansion of induced pluripotent stem cells, wherein the carrier is configured for suspension in a bioreactor, and for protecting the cells from exposure to hydrodynamic shear generated by fluid motion in a bioreactor, comprising:
  a substrate comprising two outer surfaces, wherein one or more structured indentations are present on the two outer surfaces;
  wherein the two outer surfaces comprise a biomolecular coating, the carrier has a length of about 6.5 mm, a width of about 6.5 mm, and a height of about 0.5 mm and each of the structured indentations has a major axis of about 0.45 mm, a minor axis of about 0.45 mm and a depth of about 0.2 mm.

25. The carrier of claim 24, wherein the biomolecular coating comprises proteins or peptides.

26. A carrier for expansion of induced pluripotent stem cells, wherein the carrier is configured for suspension in a bioreactor, and for protecting the cells from exposure to hydrodynamic shear generated by fluid motion in a bioreactor, comprising:
  a substrate comprising two outer surfaces, wherein one or more structured indentations are present on the two outer surfaces; wherein the two outer surfaces are modified with one or more of corona discharge treatment, gas plasma treatment, or chemical functionalization to form modified surfaces, and
  a biomolecular coating disposed on the two modified surfaces, the carrier has a length of about 6.5 mm, a width of about 6.5 mm, and a height of about 0.5 mm and each of the structured indentations has a major axis of about 0.45 mm, a minor axis of about 0.45 mm and a depth of about 0.2 mm.

27. The carrier of claim 26, wherein the gas plasma treatment comprises plasma treatment with one or more of the gases comprising oxygen, nitrogen, ammonia, carbon dioxide or combinations thereof.

* * * * *